(12) United States Patent
Carroll et al.

(10) Patent No.: US 7,872,023 B2
(45) Date of Patent: Jan. 18, 2011

(54) KAPPA OPIOID RECEPTOR LIGANDS

(75) Inventors: Frank Ivy Carroll, Research Triangle Park, NC (US); Hernan A. Navarro, Research Triangle Park, NC (US); Lawrence E. Brieaddy, Research Triangle Park, NC (US); Scott P. Runyon, Research Triangle Park, NC (US); James B. Thomas, Efland, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 1603 days.

(21) Appl. No.: 11/059,390

(22) Filed: Feb. 17, 2005

(65) Prior Publication Data

US 2006/0183743 A1    Aug. 17, 2006

(51) Int. Cl.
*A61K 31/506*   (2006.01)
*A61K 31/4545*  (2006.01)
*A61K 31/445*   (2006.01)
*A61P 25/30*    (2006.01)

(52) U.S. Cl. .................. 514/319; 514/277; 514/279; 514/338; 514/411

(58) Field of Classification Search ............ 514/241, 514/256, 317, 318, 277, 279, 319, 338, 411
See application file for complete search history.

(56) References Cited

U.S. PATENT DOCUMENTS

| | | | |
|---|---|---|---|
| 4,891,379 A | 1/1990 | Zimmerman et al. | |
| 5,128,118 A | 7/1992 | Carroll et al. | |
| 5,141,959 A | 8/1992 | Carroll et al. | |
| 5,298,499 A | 3/1994 | Carroll et al. | |
| 5,380,848 A | 1/1995 | Kuhar et al. | |
| 5,413,779 A | 5/1995 | Kuhar et al. | |
| 5,457,208 A * | 10/1995 | Portoghese et al. ......... 546/35 |
| 5,496,953 A | 3/1996 | Kuhar et al. | |
| 5,736,123 A | 4/1998 | Carroll | |
| 5,831,095 A | 11/1998 | Gonzalez et al. | |
| 5,935,953 A | 8/1999 | Kuhar et al. | |
| 6,123,917 A | 9/2000 | Carroll | |
| 6,329,520 B1 | 12/2001 | Carroll et al. | |
| 6,358,492 B1 | 3/2002 | Kuhar et al. | |
| 6,416,735 B1 | 7/2002 | Carroll et al. | |
| 6,479,509 B1 | 11/2002 | Carroll | |
| 6,531,481 B2 | 3/2003 | Carroll et al. | |
| 6,531,483 B1 | 3/2003 | Kuhar et al. | |
| 6,538,010 B1 | 3/2003 | Carroll | |
| 6,552,032 B2 | 4/2003 | Carroll et al. | |
| 6,559,159 B2 | 5/2003 | Carroll et al. | |
| 6,593,348 B2 | 7/2003 | Carroll et al. | |
| 6,706,880 B2 | 3/2004 | Carroll et al. | |
| 2002/0132828 A1 | 9/2002 | Carroll et al. | |
| 2002/0188003 A1 | 12/2002 | Kuhar et al. | |
| 2003/0158415 A1 | 8/2003 | Carroll et al. | |
| 2003/0176434 A1 | 9/2003 | Carroll | |
| 2003/0203934 A1 | 10/2003 | Kuhar et al. | |
| 2004/0146518 A1 | 7/2004 | Carroll et al. | |

FOREIGN PATENT DOCUMENTS

WO   WO 02/053533 A2   7/2002
WO   WO 2004/082623 A2   9/2004

OTHER PUBLICATIONS

Carroll, "Pharmacological properties of JDTic: a novel n-opioid receptor antagonist", European Journal of Pharmacology, 2004, 501, pp. 111-119.*
U.S. Appl. No. 11/272,492, filed Nov. 14, 2005, Carroll.
U.S. Appl. No. 12/105,814, filed Apr. 18, 2008, Carroll, et al.
U.S. Appl. No. 09/623,872, filed Oct. 17, 2000, Carroll et al.
U.S. Appl. No. 11/189,068, filed Jul. 26, 2005, Carroll et al.
U.S. Appl. No. 11/113,158, filed Apr. 25, 2005, Carroll et al.
U.S. Appl. No. 10/986,352, filed Nov. 12, 2004, Kuhar et al.
U.S. Appl. No. 10/259,780, filed Sep. 30, 2002, Carroll et al.
U.S. Appl. No. 09/537,668, filed Mar. 29, 2000, Carroll et al.
U.S. Appl. No. 60/107,902, filed Nov. 10, 1998, Carroll.
U.S. Appl. No. 08/701,503, filed Aug. 22, 1996, Boja et al.
U.S. Appl. No. 08/506,541, filed Jul. 24, 1995, Kuhar et al.
U.S. Appl. No. 11/863,587, filed Sep. 28, 2007, Kuhar et al.
U.S. Appl. No. 12/551,072, filed Aug. 31, 2009, Carroll.
Australian Office Action issued Sep. 20, 2010, in Application Serial No. 2006214118.

* cited by examiner

*Primary Examiner*—Sreeni Padmanabhan
*Assistant Examiner*—Sahar Javanmard
(74) *Attorney, Agent, or Firm*—Oblon, Spivak, McClelland, Maier & Neustadt, L.L.P.

(57) ABSTRACT

Kappa opioid receptor antagonists are provided that yield significant improvements in functional binding assays to kappa opioid receptors, and the use of these antagonists in treatment of disease states that are ameliorated by binding of the kappa opioid receptor such as heroin or cocaine addictions.

13 Claims, 7 Drawing Sheets

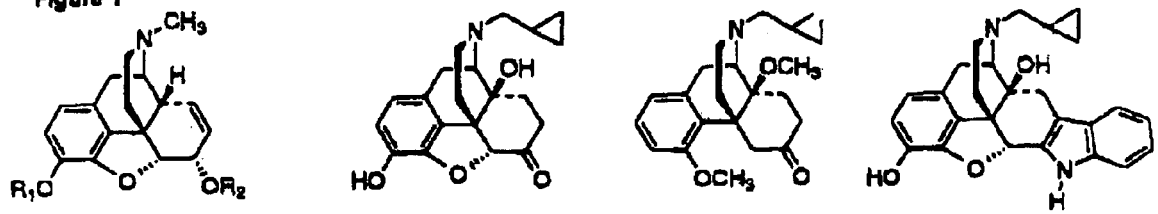
Figure 1
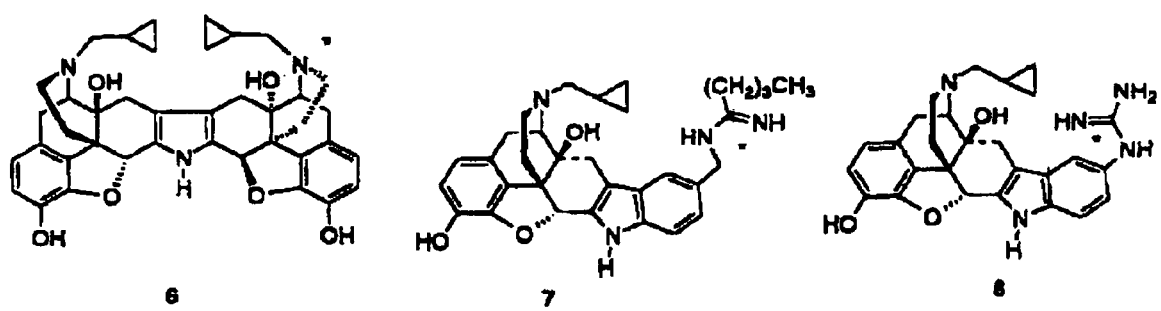
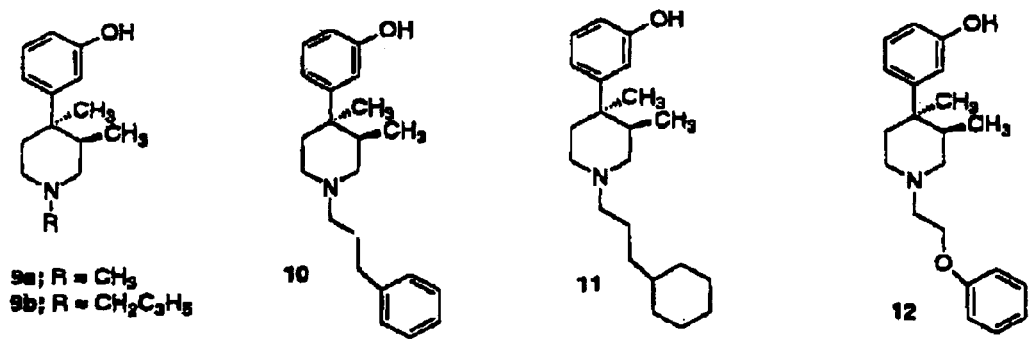
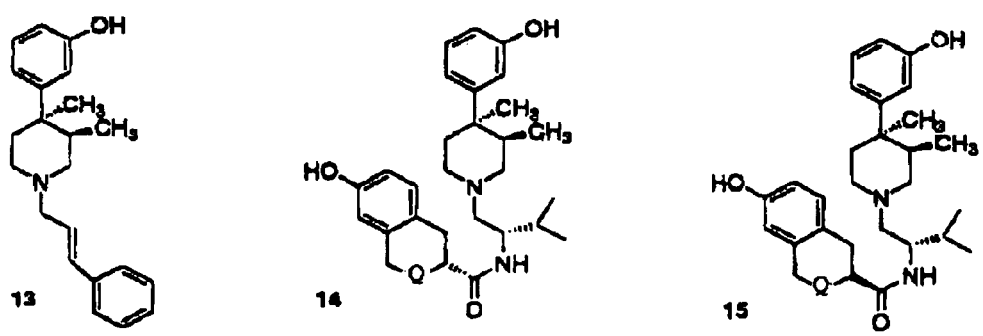

Reagents and conditions: (a) diethylcarbonate, THF, NaH; (b) $H_2$, Pd/C, EtOH, $FeCl_3$; (c) MeOH, NaOH; (d) $SOCl_2$,
Toluene; (e) EtLi, (3aR-cis)-3,3a,8,8a-tetrahydro-2H-indeno[1,2-d]oxazol-2-one (2.10),THF; (f) LiOOH, 3:1 THF/$H_2O$,
(g) BOP, TEA, THF, room temp; (h) $BBr_3$, $CH_2Cl_2$, -78 °C Reagents and conditions: (a) NaH, DMF; (b) MeOH, KOH; (c) P$_2$O$_5$, toluene, Celite; (d) Methylcyanoformate, LDA, HMPA, THF; (e) TFA, Et$_3$SiH; (f) KOH, MeOH; (g) Oxalyl chloride, CH$_2$Cl$_2$; (h) EtLi, (3aR-cis)-3,3a,8,8a-tetrahydro-2H-indeno[1,2-d]oxazol-2-one (3.9),THF; (i) LiOH, 3:1 THF/H$_2$O, (j) N-[(2'S)-Amino-3'-methylbutyl]-(3R,4R)-trans-dimethyl-4-(3-hydroxyphenyl)piperidine (3.13), BOP, TEA, THF, room temp; (h) BBr$_3$, CH$_2$Cl$_2$, -78 °C to 0 °C

Figure 4

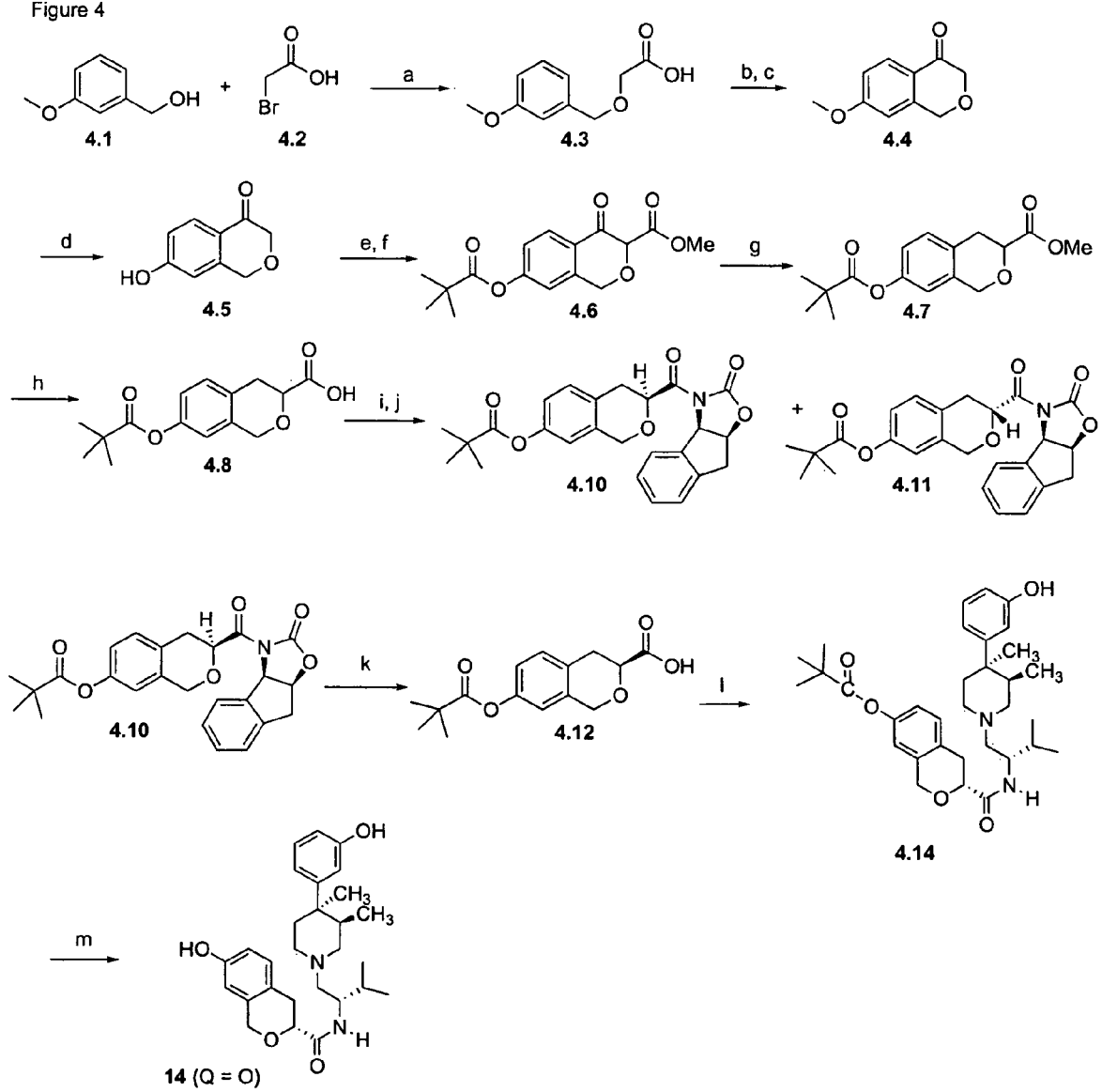

Reagents and conditions: (a) NaH, THF; (b) Oxalyl chloride, $CH_2Cl_2$; (c) $SnCl_4$, Chlorobenzene, 0 ¡C; (d) NaSEt, DMF, reflux; (e) Pivaloyl chloride, TEA; (f) Methyl cyanoformate, LDA, HMPA, THF; (g) TFA, $Et_3SiH$; (h) $NaHCO_3$, MeOH; (i) Oxalyl chloride, $CH_2Cl_2$; (j) EtLi, (3aR-cis)-3,3a,8,8a-tetrahydro-2H-indeno[1,2-d]oxazol-2-one (4.9),THF; (k) LiOH, 3:1 THF/$H_2O$, 0 ¡C (l) N-[(2'S)-Amino-3'-methylbutyl]-(3R,4R)-trans-dimethyl-4-(3-hydroxyphenyl)piperidine (4.13), BOP, TEA, THF, room temp; (m) 3M HCl, dioxane.

KAPPA OPIOID RECEPTOR LIGANDS

BACKGROUND OF THE INVENTION

1. Field of Invention

The present invention relates to compounds that bind with high affinity and/or specificity to kappa opioid receptors.

2. Discussion of the Background

The study of compounds exerting their actions via the opioid receptor system has continued for nearly eight decades. Though this has been a broad effort, the fundamental driving force for this endeavor relates to the elimination or reduction of the side-effect profile produced by the most frequently used or abused opiates morphine (1) and heroin (2) in FIG. 1. Among the many side effects produced by compounds 1 and 2, addiction, tolerance and respiratory depression are of greatest concern when heroin abuse is considered. Though its use waned in the late 70s, increases in both the purity and availability of this drug have promoted a serious resurgence of illegal use. In the study and treatment of substance abuse, antagonists for the opioid receptors like naltrexone (3) (FIG. 1) have played a prominent role. In recent years, researchers studying the physiological mechanisms underlying addiction have sought antagonists selective for each of the three opioid receptor subtypes mu, delta and kappa. Extensive research efforts along these lines lead to the discovery of several such compounds with examples including cyprodime (mu, 4), naltrindole (delta, 5) and nor-binaltorphimine (kappa, 6) (FIG. 1). Of the three, the kappa receptor has only begrudgingly yielded antagonists and, of the known examples, all stem from modification of the prototype, nor-binaltorphimine (nor-BNI, 6).

Portoghese in his pioneering work provided not only the second and third generation kappa antagonists 5'-[(N2-butylamidino)methyl]naltrindole (7) and C5'-guanidinylnaltrindole (GNTI, 8) but also convincing evidence that the Glu297 residue in transmembrane helix 6 of the kappa receptor is the principle address site influencing the kappa selectivity found in 6-8 (FIG. 1). In terms of the message address concept as applied by Portoghese to opioid small-molecules, it is the pendant amine functionality (noted by asterisks in the chart) that functions as the kappa address element for compounds 6-8 by interacting with the Glu297 residue which is present in the kappa but not in the mu receptor.

In terms of substance abuse treatment, antagonists selective for the kappa receptor have been the least studied primarily due to the limited bio-availability of 6 and its analogs. However, mounting evidence that the endogenous kappa opioid system opposes the actions of mu agonists like 2 suggests that antagonists selective for the kappa receptor system could suppress or eliminate the symptoms of withdrawal which arise from an overactive kappa receptor system and thus could promote abstinence and prevent relapse. Therefore, the development of novel kappa antagonists possessing improved pharmacokinetic profiles would be of great value.

As is obvious from the examples above, the morphinan substructure of 3 has served as the preeminent template upon which selective antagonists have been constructed. Contrary to these efforts, our work in this field started from the relatively unstudied N-substituted trans-(3,4)-dimethyl-4-(3-hydroxyphenyl)piperidine class of opioid antagonist discovered by Zimmerman et al. Compounds like 9a and 9b (FIG. 1) were novel opioid antagonists because their intrinsic antagonist activity was not mediated by the structure of their N-substituent (i.e. the N-methyl (9a) and N-cyclopropylmethyl (9b) analogs in the phenylpiperidine series are both pure antagonists). Indeed, no N-substituent has been discovered which converts this series of compound into an agonist. Compounds 10-12 (FIG. 1) represent some of the structures tried to date. In this connection we recently demonstrated that compounds bearing the trans-cinnamyl N-substituent, as found in 13 (FIG. 1), most closely reproduced the potency at the mu opioid receptor of the flexible N-substituted analogs (10-12). In fact, the comparable mu receptor potencies demonstrated by analogs trans-(3,4)-dimethyl-4-(3-hydroxyphenyl)piperidine possessing the trans-cinnamyl moiety lead us to speculate that in their biologically active conformation, compounds such as 10-12 have the connecting chain and appended ring in their N-substituent extended away from the piperidine nitrogen in a manner consistent with the trans-cinnamyl skeleton like that found in 13.

In more recent studies comparing opioid receptor potency and selectivity to N-substituent changes in this series of antagonists, we discovered 14-18, where Q is $CH_2$, O, S, SO, or $SO_2$ (FIG. 1). These compounds were obtained from the screening of libraries of compounds which were biased for opioid antagonist activity by incorporation of trans-(3,4)-dimethyl-4-(3-hydroxyphenyl)piperidine into each ligand. In biological testing those compounds (14-18) were found to possess kappa opioid receptor subtype selectivity in functional binding assays.

SUMMARY OF THE INVENTION

It is an object of the invention to provide compounds which bind to kappa opioid receptors with high affinity.

It is another object of the invention to provide compounds which bind to kappa opioid receptors with high specificity.

It is another object of the invention to provide compounds which bind to kappa opioid receptors with high affinity and specificity in functional assays.

The objects of the present invention, and others, are accomplished with compounds of the structures described herein, particularly compounds 14-18, which have the above advantages.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 2-4: examples of synthetic routes to compounds (14-18);

DETAILED DESCRIPTION OF THE INVENTION

Figure 1:
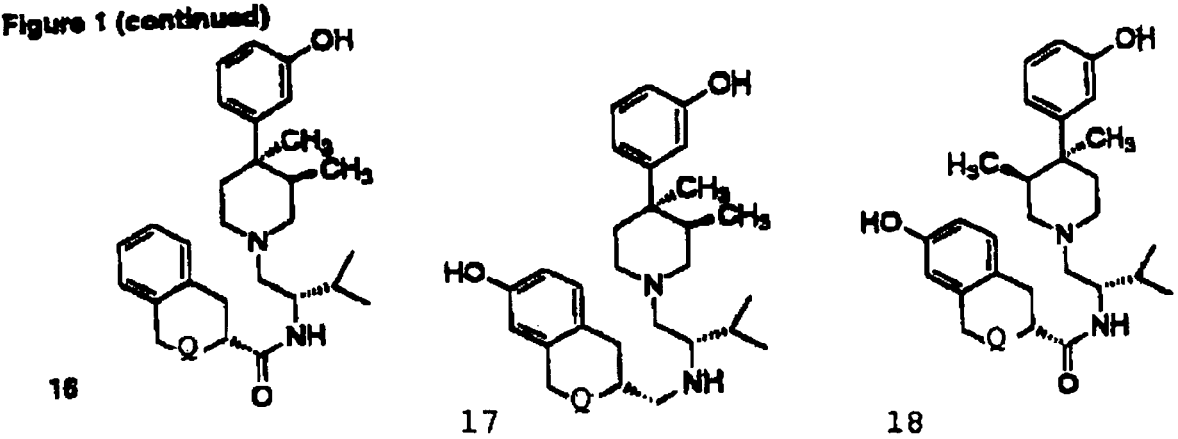
FIG. 1: chemical structure of compounds (1)-(18)

The present invention provides kappa opioid antagonists that bind to kappa opioid receptors with high affinity and/or specificity. Compounds of the present invention are those represented by the formula (I):

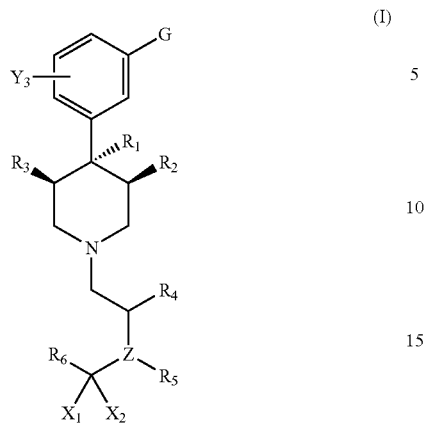
(I)

wherein G is H, OH, OCOC$_{1-8}$ alkyl, CONH$_2$, NHCHO, NH$_2$, NHSO$_2$C$_{1-8}$ alkyl, or NHCO$_2$C$_{1-8}$ alkyl R$_1$ is C$_{1-8}$ alkyl, or one of the following structures:

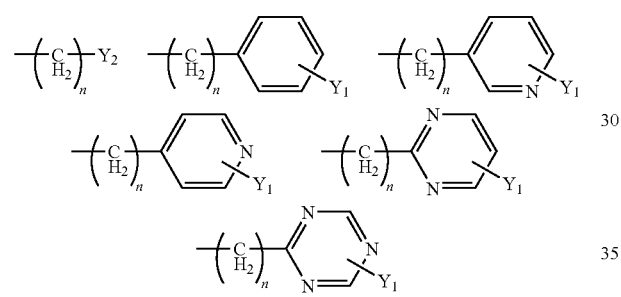

Y$_1$ is H, OH, Br, Cl, F, CN, CF$_3$, NO$_2$, N$_3$, OR$_8$, CO$_2$R$_9$, C$_{1-6}$alkyl, NR$_{10}$R$_{11}$, NHCOR$_{12}$, NHCO$_2$R$_{12}$, CONR$_{13}$R$_{14}$, or CH$_2$(CH$_2$)$_n$Y$_2$;

Y$_2$ is H, CF$_3$, CO$_2$R$_9$, C$_{1-6}$alkyl, NR$_{10}$R$_{11}$, NHCOR$_{12}$, NHCO$_2$R$_{12}$, CONR$_{13}$R$_{14}$, CH$_2$OH, CH$_2$OR$_8$, or COCH$_2$R$_9$;

Y$_3$ is H, OH, Br, Cl, F, CN, CF$_3$, NO$_2$, N$_3$, OR$_8$, CO$_2$R$_9$, C$_{1-6}$ alkyl, NR$_{10}$R$_{11}$, NHCOR$_{12}$, NHCO$_2$R$_{12}$, CONR$_{13}$R$_{14}$, or CH$_2$(CH$_2$)$_n$Y$_2$;

R$_2$ is H, C$_{1-8}$ alkyl, C$_{3-8}$ alkenyl, C$_{3-8}$ alkynyl or CH$_2$aryl substituted by one or more groups Y$_1$;

R$_3$ is H, C$_{1-8}$ alkyl, C$_{3-8}$ alkenyl, C$_{3-8}$ alkynyl or CH$_2$aryl substituted by one or more groups Y$_1$;

wherein R$_2$ and R$_3$ may be bonded together to form a C$_{2-8}$ alkyl group;

R$_4$ is hydrogen, C$_{1-8}$ alkyl, CO$_2$C$_{1-8}$ alkylaryl substituted by one or more groups Y$_1$, CH$_2$aryl substituted by one or more groups Y$_1$ or CO$_2$C$_{1-8}$ alkyl;

Z is N, O or S; when Z is O or S, there is no R$_5$

R$_5$ is H, C$_{1-8}$ alkyl, C$_{3-8}$ alkenyl, C$_{3-8}$ alkynyl, CH$_2$CO$_2$C$_{1-8}$ alkyl, CO$_2$C$_{1-8}$ alkyl or CH$_2$aryl substituted by one or more groups Y$_1$; (when Z is O or S, there is no R$_5$)

n is 0, 1, 2 or 3;

R$_6$ is a group selected from the group consisting of structures (a)-(p):

 (a)

 (b)

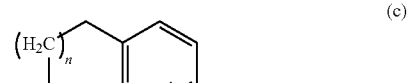 (c)

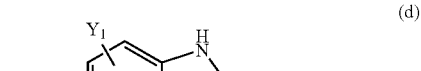 (d)

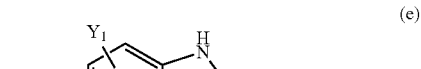 (e)

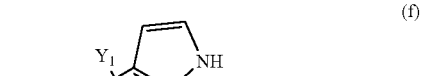 (f)

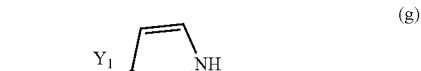 (g)

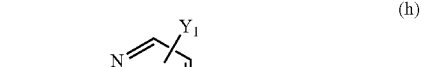 (h)

-continued (i) 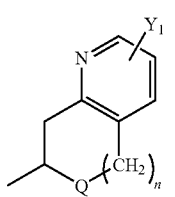

(j) 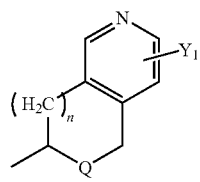

(k) 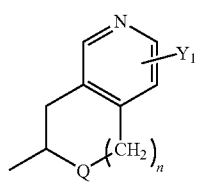

(l) 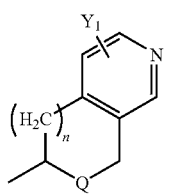

(m) 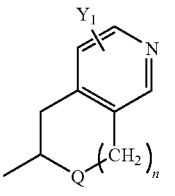

(n) 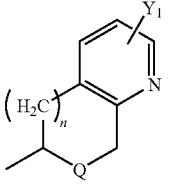

(o) 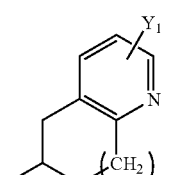

(p) 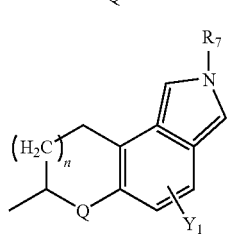

Q is $CH_2$, O, S, SO, or $SO_2$;
$X_1$ is hydrogen, $C_{1-8}$ alkyl, $C_{3-8}$alkenyl, or $C_{3-8}$alkynyl;

$X_2$ is hydrogen, $C_{1-8}$alkyl, $C_{3-8}$alkenyl, or $C_{3-8}$alkynyl;
or $X_1$ and $X_2$ together form =O, =S, or =NH;
$R_7$ is H, $C_{1-8}$alkyl, $CH_2$aryl substituted by one or more substituents $Y_1$, $NR_{10}R_{11}$, $NHCOR_{12}$, $NHCO_2R_{13}$, $CONR_{14}R_{15}$, $CH_2(CH_2)_nY_2$, or $C(=NH)NR_{16}R_{17}$;

$R_8$ is H, $C_{1-8}$alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, $C_{1-6}$alkyl;

$R_9$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{10}$ is H, $C_{1-8}$ alkyl, $CH_2$ aryl substituted by one or more substituents H, OH, Br, Cl, F, CN, $CF_3$, $NO_2$, $N_3$; $C_{1-6}$ alkyl, or $CH_2(CH_2)_nY_2'$; wherein $Y_2'$ is H, $CF_3$, or $C_{1-6}$alkyl;

$R_{11}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{12}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{13}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{14}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{15}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{16}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{17}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

and pharmaceutically acceptable salts thereof.

Preferably, the compounds of the present invention are those represented by the formula I as shown above, wherein G, $R_1$, $R_4$, $R_5$, $Y_1$, $Y_2$, Z, n, $X_1$, $X_2$, Q and $R_7$-$R_{17}$ are as indicated above;

$Y_3$ is H;

$R_2$ and $R_3$ are each, independently, H, $C_{1-8}$ alkyl, $C_{3-8}$ alkenyl, $C_{3-8}$ alkynyl, or $CH_2$aryl substituted by one or more substituents $Y_1$; and $R_6$ is a group having a formula selected from the group consisting of structures (a)-(p) above.

More preferably, the compounds of the present invention are those represented by the formula I as shown above, wherein G, $Y_1$, $Y_2$, $R_4$, $R_5$, Z, n, $X_1$, $X_2$, Q and $R_8$-$R_{15}$ are as indicated above;

$R_1$ is $C_{1-8}$ alkyl, or one of the following structures

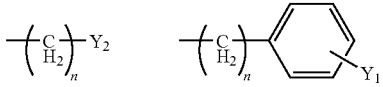

$Y_3$ is H;

$R_2$ and $R_3$ are each, independently, H or $C_{1-8}$ alkyl, wherein $R_2$ and $R_3$ cannot both be H at the same time;

$R_6$ is a formula selected from the structures (a)-(p) shown above; and $R_7$ is H, $C_{1-8}$ alkyl, $CH_2$aryl substituted by one or more substituents $Y_1$, $NR_{10}R_{11}$, $NHCOR_{12}$, $NHCO_2R_{13}$, $CONR_{14}R_{15}$, or $CH_2(CH_2)_nY_2$.

Still more preferably, the compound of the present invention are those represented by the formula I as shown above, wherein G, $Y_1$, Z, n, $X_1$, $X_2$, Q and $R_8$-$R_{15}$ are as noted above;

$R_1$ is $C_{1-8}$ alkyl;

$Y_2$ is H, $CF_3$, $CO_2R_9$, $C_{1-6}$ alkyl, $NR_{10}R_{11}$, $NHCOR_{12}$, $NHCO_2R_{12}$, $CONR_{13}R_{14}$, $CH_2OH$, $CH_2OR_8$, or $COCH_2R_9$;

$Y_3$ is H;

$R_2$ and $R_3$ are each, independently, H or methyl, wherein $R_2$ and $R_3$ cannot both be H at the same time;

$R_4$ is H, $C_{1-8}$ alkyl, $CO_2C_{1-8}$alkyl, or aryl substituted by one or more substituents $Y_1$ and the stereocenter adjacent to $R_4$ is in an (S) configuration;

$R_5$ is H, $C_{1-8}$ alkyl, or $CH_2CO_2C_{1-8}$ alkyl;

$R_6$ is a group having a formula selected from the group consisting of structures (a)-(c) and (h)-(p); and $R_7$ is H, $C_{1-8}$alkyl, $CH_2$aryl substituted by one or more substituents $Y_1$, $NR_{10}R_{11}$, $NHCOR_{12}$, $NHCO_2R_{13}$, $CONR_{14}R_{15}$, or $CH_2(CH_2)_nY_2$.

Most preferably, the compounds of the present invention are those represented by the formula I as shown above, wherein G, $Y_1$, Z, n, $X_1$, $X_2$, Q and $R_8$-$R_{14}$ are as indicated above;

$R_1$ is methyl, $Y_2$ is H, $CF_3$, $CO_2R_9$, $C_{1-6}$ alkyl, $NR_{10}R_{11}$, $NHCOR_{12}$, $NHCO_2R_{12}$, $CONR_{13}R_{14}$, $CH_2OH$, $CH_2OR_8$, or $COCH_2R_9$;

$Y_3$ is H;

$R_2$ and $R_3$ are each H or methyl, such that when $R_2$ is H, $R_3$ is methyl and vice versa;

$R_4$ is $C_{1-8}$ alkyl, or $CO_2C_{1-8}$ alkyl, and the stereocenter adjacent to $R_4$ has a configuration of (S);

$R_5$ is H;

$R_6$ is a group having a formula selected from the group consisting of structures (a) and (b); and $R_7$ is H, $C_{1-8}$ alkyl, $CH_2$aryl substituted by one or more substituents $Y_1$ or $CH_2(CH_2)_nY_2$.

A most preferred set of compounds are the compounds of formula 14-18 as shown in FIG. 1, where Q is $CH_2$, O, S, SO, or $SO_2$.

As used throughout this disclosure, the terms "alkyl group" or "alkyl radical" encompass all structural isomers thereof, such as linear, branched and cyclic alkyl groups and moieties. Unless stated otherwise, all alkyl groups described herein may have 1 to 8 carbon atoms, inclusive of all specific values and subranges therebetween, such as 2, 3, 4, 5, 6, or 7 carbon atoms.

The alkenyl group or alkynyl group may have one or more double or triple bonds, respectively. As will be readily appreciated, when an alkenyl or alkynyl group is bonded to a heteroatom a double or triple bond is not formed with the carbon atom bonded directly to the heteroatom.

The aryl group is a hydrocarbon aryl group, such as a phenyl, naphthyl, phenanthryl, anthracenyl group, which may have one or more $C_{1-4}$ alkyl group substituents.

The compounds of the present invention are opiates which are preferably antagonists that are selective for the kappa receptor. The κ/μ selectivity may be at least 2:1, but is preferably higher, e.g., at least 5:1, 10:1, 25:1, 50:1, 100:1, 200:1 or even 500:1. The κ/δ selectivity may be at least 2:1, but is preferably higher, e.g., at least 5:1, 10:1, 25:1, 50:1, 100:1, 200:1, 250:1, 500:1 or even 1000:1.

Figure 2:
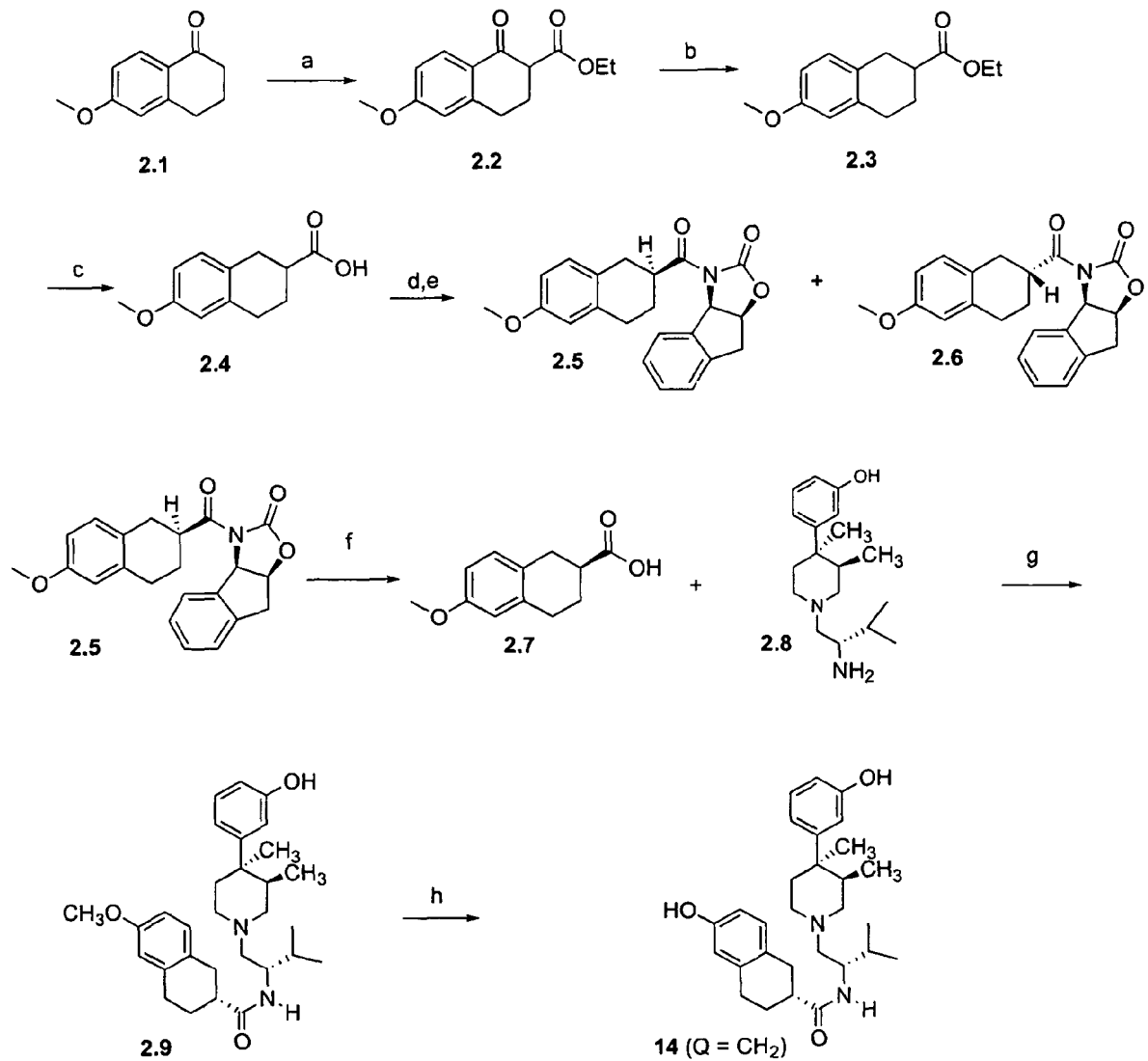

The compounds 14 and 15 Q=$CH_2$ of the present invention may be synthesized, for example, in accordance with the reaction sequence shown in FIG. 2. Condensation of the tetralone 2.1 with diethylcarbonate gives the keto carboethoxy ester 2.2. Subjection of 2.2 to catalytic reduction gives 2.3. Hydrolysis of 2.3 affords the acid 2.4. Treatment of 2.4 with thionyl chloride followed by the lithium salt of 2.10 gives a mixture of 2.5 and 2.6, which are separated by chromatography. Treatment of 2.5 with lithium peroxide in a THF/$H_2O$ mixture gives the acid 2.7. Coupling the acid with 2.10 gives the phenol-protected analog 2.9. Subjection of 2.9 to boron tribromide in methylene chloride at −78° C. gives the desired 14 (Q=$CH_2$). Compound 15 (Q=$CH_2$) is prepared by a similar route starting with 2.6.

Figure 3:
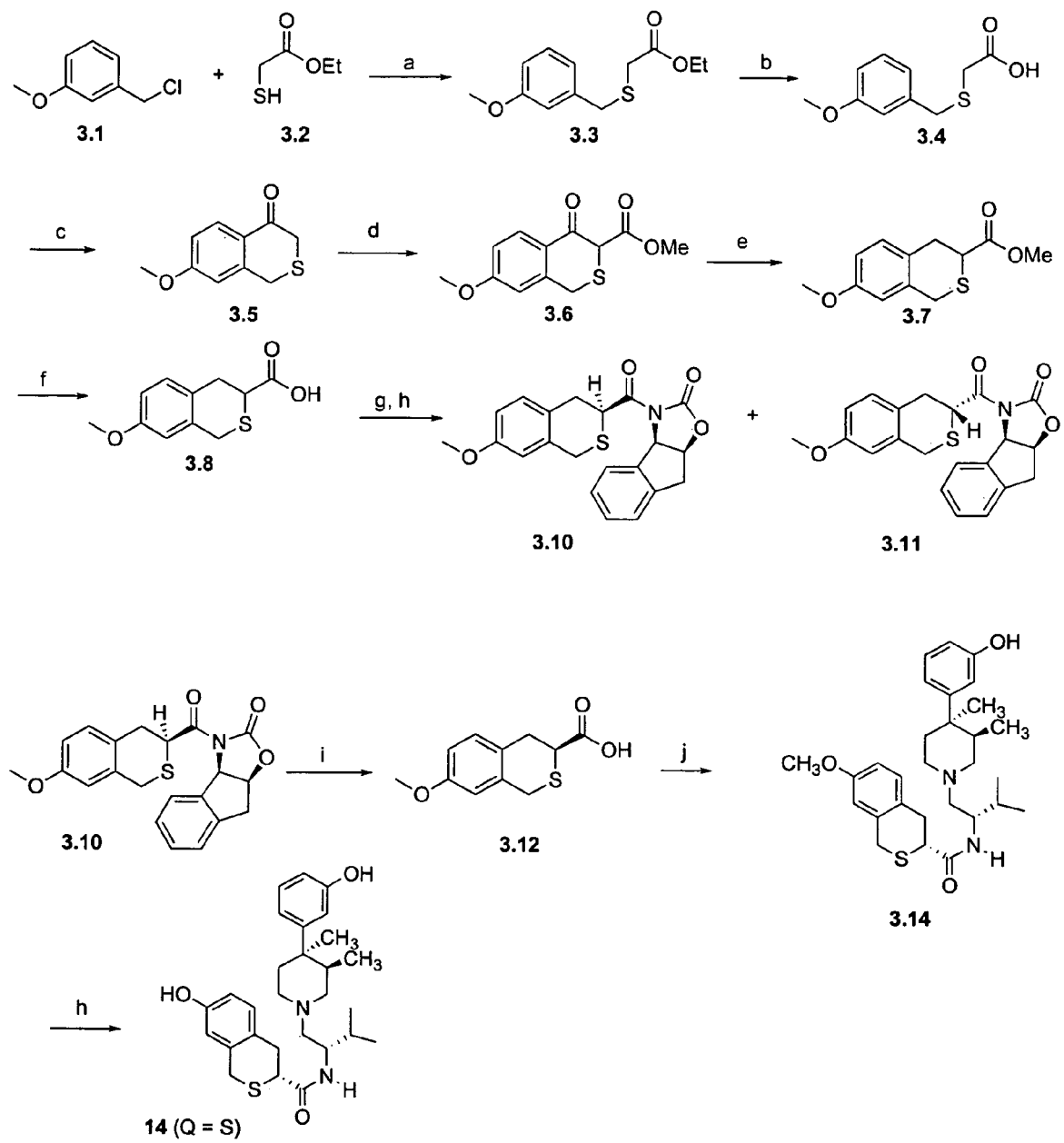

The compounds 14 and 15 (Q=S) of the present invention may be synthesized, for example, in accordance with the reaction sequence shown in FIG. 3. Nucleophilic displacement of benzyl chloride 3.1 with ethyl mercaptoacetate 3.2 affords sulfide 3.3. Hydrolysis of the ester with KOH in MeOH provides the acid 3.4. Cyclodehydration of the acid 3.4 using phosphorous pentoxide gives isothiochromanone 3.5. Condensation of the isothiochromanone 3.5 with methyl cyanoformate gives the keto carbomethoxy ester 3.6. Reduction of the ketone to give 3.7 is accomplished using triethylsilane in TFA. Hydrolysis of the ester with KOH provides the acid 3.8. Treatment of 3.8 with oxalyl chloride followed by the lithium salt of 3.9 gives a mixture of 3.10 and 3.11 which are separated by chromatography. Hydrolysis of 3.10 with lithium hydroxide gives the acid 3.12. Coupling of the acid 3.12 with the amino compound 3.13 gives the phenol protected analog 3.14. Subjection of 3.14 to boron tribromide in methylene chloride at −78° C. gives the desired 14 (Q=S). Compound 15 (Q=S) is prepared by a similar route starting with 3.11.

The compounds 14 and 15 (Q=O) of the present invention may be synthesized, for example in accordance with the reaction sequence shown in FIG. 4. Alkylation of benzyl alcohol 4.1 with bromoacetic acid 4.2 in THF provides the ether 4.3. Acid halide formation of 4.3 followed by intramolecular acylation using $SnCl_4$ at 0° C. gives the isochromanone 4.4. Deprotection to give the phenol 4.5 is accomplished using sodium ethanethiolate in DMF at reflux. Reprotection of phenol 4.5 with pivaloyl chloride and TEA in THF followed by condensation of the resulting isochromanone with methyl cyanoformate gives the keto carbomethoxy ester 4.6. Reduction of the ketone to give 4.7 is accomplished using triethylsilane in TFA. Selective hydrolysis of the methyl ester provides the acid 4.8. Treatment of 4.8 with oxalyl chloride followed by the lithium salt of 4.9 gives a mixture of 4.10 and 4.11 which are separated by chromatography. Hydrolysis of 4.10 with lithium hydroxide gives the acid 4.12. Coupling of the acid 4.12 with the amino compound 4.13 gives the phenol protected analog 4.14. Cleavage of the pivaloyl protecting group is accomplished with 3M HCl in dioxane to give 14 (Q=O). Compound 15 (Q=O) is prepared by a similar route starting with 4.11.

The compounds of the present invention may be in the form of a pharmaceutically acceptable salt via protonation of the amines with a suitable acid. The acid may be an inorganic acid or an organic acid. Suitable acids include, for example, hydrochloric, hydroiodic, hydrobromic, sulfuric, phosphoric, citric, acetic, fumaric, tartaric, and formic acids.

The receptor selectivities discussed above are determined based on the binding affinities at the receptors indicated or their selectivity in opioid functional assays.

The compounds of the present invention may be used to bind opioid receptors. Such binding may be accomplished by contacting the receptor with an effective amount of the inventive compound. Of course, such contacting is preferably conducted in an aqueous medium, preferably at physiologically relevant ionic strength, pH, etc.

The inventive compounds may also be used to treat patients having disease states which are ameliorated by binding opioid receptors or in any treatment wherein temporary suppression of the kappa opioid receptor system is desired. Such disease states include opiate addiction (such as heroin addiction), cocaine, nicotine, or ethanol addiction. The compounds of the present invention may also be used as cytostatic agents, as antimigraine agents, as immunomodulators, as immunosuppressives; as antiarthritic agents, as antiallergic agents, as virucides, to treat diarrhea, as antipsychotics, as antischizophrenics, as antidepressants, as uropathic agents, as antitussives, as antiaddictive agents, as anti-smoking agents, to treat alcoholism, as hypotensive agents, to treat and/or prevent paralysis resulting from traumatic ischemia, general neuroprotection against ischemic trauma, as adjuncts to nerve growth factor treatment of hyperalgesia and nerve grafts, as anti-diuretics, as stimulants, as anti-convulsants, or to treat obesity. Additionally, the present compounds can be used in the treatment of Parkinson's disease as an adjunct to L-dopa for treatment of dyskinesia associated with the L-dopa treatment.

The compounds may be administered in an effective amount by any of the conventional techniques well-established in the medical field. For example, the compounds may be administered orally, intraveneously, or intramuscularly. When so administered, the inventive compounds may be combined with any of the well-known pharmaceutical carriers and additives that are customarily used in such pharmaceutical compositions. For a discussion of dosing forms, carriers, additives, pharmacodynamics, etc., see Kirk-Othmer Encyclopedia of Chemical Technology, Fourth Edition, Vol. 18, 1996, pp. 480-590, incorporated herein by reference. The patient is preferably a mammal, with human patients especially preferred. Effective amounts are readily determined by those of ordinary skill in the art. Studies by the present inventors show no toxicity and no lethality for the present compounds at amounts up to 300 mg/kg in mice.

The compounds of the present invention can be administered as a single dosage per day, or as multiple dosages per day. When administered as multiple dosages, the dosages can be equal doses or doses of varying amount, based upon the time between the doses (i.e. when there will be a longer time between doses, such as overnight while sleeping, the dose administered will be higher to allow the compound to be present in the bloodstream of the patient for the longer period of time at effective levels). Preferably, the compound and compositions containing the compound are administered as a single dose or from 2-4 equal doses per day.

Suitable compositions containing the present compounds further comprise a physiologically acceptable carrier, such as water or conventional pharmaceutical solid carriers, and if desired, one or more buffers and other excipients.

EXAMPLES

Having generally described this invention, a further understanding can be obtained by reference to certain specific examples which are provided herein for purposes of illustration only and are not intended to be limiting unless otherwise specified.

Chemistry

Synthesis of 14 and 15 (Q=CH$_2$)

6-Methoxy-1-oxo-1,2,3,4-tetrahydronaphthalene-2-carboxylic acid ethyl ester. NaH (3.4 g, 60% in mineral oil, 83.3 mmol) was washed with hexanes (3×70 mL) and THF (1×30 mL) in an oven dried 3 neck round-bottomed flask. Diethyl carbonate (5.5 mL, 45.4 mmol) was added to the NaH/THF suspension in anhydrous THF (20 mL) and the slurry was heated at reflux under N$_2$. 6-Methoxy-1-tetralone (4 g, 22.7 mmol) in THF (40 mL) was added dropwise via an addition funnel to the suspension at reflux. The reaction mixture was then heated at reflux for 2 days. The solution was cooled to room temperature and glacial AcOH (3.6 mL) was added in a dropwise manner. Et$_2$O (150 mL) was then added and the organic layer was washed with saturated NaCl solution (5×25 mL), dried (MgSO$_4$), and concentrated under reduced pressure to provide a crude brown oil (6.0 g). The oil was subjected to medium pressure chromatography on silica (CHCl$_3$) to provide a dark oil which solidified upon standing (5.17 g, 91.8% yield). The solid was recrystallized from EtOAc/hexane to provide a white solid. mp 58-60° C. $^1$H-NMR (300 MHz, CDCl$_3$) δ 1.27-1.36 (t, 3H), 2.20-3.56 (m, 5H), 3.85 (s, 3H), 4.23-4.28 (m, 2H), 6.70 (s, 1H), 6.77-6.85 (d, 1H), 7.72-8.03 (d, 1H).

6-Methoxy-1,2,3,4-tetrahydro-naphthalene-2-carboxylic acid ethyl ester. 10% Pd/C (195 mg) was added to a suspension of 6-methoxy-1-oxo-1,2,3,4-tetrahydronaphthalene-2-carboxylic acid ethyl ester (1.07 g, 4.32 mmol) and FeCl$_3$, (5 mg) in EtOH (30 mL) under N$_2$. The suspension was hydrogenated at 40 psi for 3 days. The suspension was filtered through a Celite pad and the filtrate was concentrated to a leave crude oil. The oil was purified using medium pressure chromatography on silica (CHCl$_3$) to provide a colorless oil (886 mg, 88.3% yield). $^1$H-NMR (300 MHz, CDCl$_3$) δ 1.28 (t, J=7.2 Hz, 3H). 1.84 (m, 1H), 2.19 (m, 1H), 2.70 (m, 1H), 2.83 (m, 2H), 2.93 (m, 2H), 3.77 (s, 3H), 4.17 (q, J=7.2 Hz, 2H), 6.62 (s, 1H), 6.69 (dd, J=8.4, 2.4 Hz, 1H), 7.01 (d, J=8.4 Hz, 1H).

6-Methoxy-1,2,3,4-tetrahydro-naphthalene-2-carboxylic acid. 6-methoxy-1,2,3,4-tetrahydro-naphthalene-2-carboxylic acid ethyl ester (868 mg, 3.74 mmol) oil was dissolved in 10 mL of 10% methanolic NaOH and heated at reflux for 18 hours. The hydrolyzed product was filtered upon cooling to provide the sodium carboxylate salt (445 mg, 1.97 mmol). The filtrate was acidified with 1N HCl, extracted with CHCl$_3$ (3×100 mL), dried (Na$_2$SO$_4$), and concentrated under reduced pressure to provide 6-methoxy-1,2,3,4-tetrahydronaphthalene-2-carboxylic acid as a white flaky solid (361 mg, 99%). The solid was recrystallized from EtOAc/hexane to provide fine white cubes. mp 151-152° C. $^1$H-NMR (300 MHz CDCl$_3$) δ 1.89 (m, 1H), 2.22 (m, 1H), 2.75-2.89 (m, 3H), 2.95-2.99 (m, 2H), 3.78 (s, 3H), 6.63 (s, 1H), 6.72, (dd, J=8.4, 2.7 Hz, 1H), 7.02 (d, J=8.4 Hz, 1H).

6-Methoxy-1,2,3,4-tetrahydronaphthalene-2-carbonyl chloride. A 2.0 M solution of thionyl chloride (7.25 mL, 14.3 mmol) in CH$_2$Cl$_2$ was added to a solution of 6-methoxy-1,2,3,4-tetrahydronaphthalene-2-carboxylic acid (0.29 g, 1.43 mmol) in toluene (20 mL). The solution was heated at reflux for 8 hours, cooled to room temperature and concentrated under reduced pressure to provide a tan solid. The acid halide was used in the next step without further purification.

(3aR-cis)-3-(6-Methoxy-1,2,3,4-tetrahydronaphthalene-2(+ and −)-carbonyl)-3,3a,8,8a-tetrahydro-2H-indeno[1,2-d] oxazol-2-one. A 0.50 M solution of ethyl lithium (3.0 mL, 1.50 mL) in benzene/cyclohexane 90:10 was added to a solution of (3aR-cis)-3,3a,8,8a-tetrahydro-2H-indeno[1,2-d]oxazol-2-one (0.25 g, 1.43 mmol) in THF (20 mL) at 0° C. under N$_2$. The suspension was allowed to stir at 0° C. for 0.5 hours and was then cooled to −78° C. A solution of 6-methoxy-1,2,3,4-tetrahydronaphthalene-2-carbonyl chloride (0.29 g, 1.43 mmol) in THF (10 mL) was then added in a dropwise manner to the −78° C. slurry. The resulting slurry was allowed to warm to room temperature over 2 hours and water (100 mL) was then added. The suspension was extracted with CH$_2$Cl$_2$ (3×100 mL). The organic extracts were combined, dried (MgSO$_4$), and concentrated under reduced pressure to provide a tan solid. The solid was purified on silica with medium pressure column chromatography (70:30 petroleum ether/Et$_2$O) to provide each of the diastereomers in approximately 50% theoretical yield. The yield improves with additional chromatography. The less polar spot was later identified as the (+) isomer while the more polar was (−).

Analysis for: (3a(R)-cis)-3-(6-Methoxy-1,2,3,4-tetrahydronaphthalene-2(+)-carbonyl)-3,3a,8,8a-tetrahydro-2H-indeno[1,2-d]oxazol-2-one. The solid was recrystallized from ethyl acetate/petroleum ether to provide a white solid (0.12 g, 46%). mp. 168-169° C. $^1$H-NMR (300 MHz, CDCl$_3$) δ 1.80-1.85 (m, 1H), 2.10-2.21 (m, 1H), 2.71-3.13 (m, 4H), 3.38 (d, J=3.3 Hz, 2H), 3.76 (s, 3H), 3.84 (m, 1H), 5.27 (m, 1H), 5.96-5.99 (d, J=9 Hz, 1H), 6.62 (s, 1H), 6.70-6.71 (dd, J=2.4, 8.1 Hz, 1H), 6.99-7.04 (dd, J=3.6, 8.4 Hz, 1H), 7.24-7.32 (m, 3H), 7.57-7.60 (d, J=7.5 Hz, 1H).

Analysis for: (3aR-cis)-3-(6-Methoxy-1,2,3,4-tetrahydronaphthalene-2(−)-carbonyl)-3,3a,8,8a-tetrahydro-2H-indeno[1,2-d]oxazol-2-one. The solid was recrystallized from ethyl acetate/petroleum ether to provide a white solid (0.13 g, 50%). mp. 162-164° C. $^1$H-NMR (300 MHz, CDCl$_3$) δ 1.85-1.98 (m, 1H), 2.12-2.18 (m, 1H), 2.84-2.95 (m, 4H), 3.40-3.41 (d, J=3.3 Hz, 2H), 3.77 (s, 3H), 3.85-3.95 (m, 1H), 5.28-5.33 (m, 1H), 5.97-5.99 (d, J=6.9 Hz, 1H), 6.57-6.69 (m, 2H), 6.95-6.98 (d, J=8.4 Hz, 1H), 7.26-7.42 (m, 3H), 7.60-7.62 (d, J=7.5 Hz, 1H).

2(+)-6-Methoxy-1,2,3,4-tetrahydronaphthalene-2-carboxylic acid. A 30% solution of hydrogen peroxide (6.96 mmol, 0.24 mL) in H$_2$O was added at 0° C. to a solution of (3aR-cis)-3-(6-methoxy-1,2,3,4-tetrahydronaphthalene-2(+)-carbonyl)-3,3a,8,8a-tetrahydro-2H-indeno[1,2-d]oxazol-2-one (0.42 g, 1.16 mmol) in 3:1 THF/H$_2$O (25 mL). Lithium hydroxide hydrate (0.098 g, 2.32 mmol) was then added to the solution in portions. The suspension was allowed to stir for 0.5 hours at 0° C. and then for 2 hours at room temperature. A 1.5 N solution of Na$_2$SO$_3$ (15 mL) was added in a dropwise manner and the biphasic solution was basified (pH ≈10) with saturated sodium bicarbonate solution. The solution was extracted (2×50 mL) with EtOAc, made acidic to pH 3 with HCl (10 M solution) and extracted (3×100 mL) with CH$_2$Cl$_2$. The organic extracts were combined, dried (MgSO$_4$), and concentrated under reduced pressure to provide a white solid. The solid was recrystallized from EtOAc/petroleum ether to provide 2(+)-6-methoxy-1,2,3,4-tetrahydronaphthalene-2-carboxylic acid as white needles (0.219 g, 92%). mp. 129-130° C. [a]$^{22}_D$+57.27° (c 0.22, CHCl$_3$) $^1$H-NMR (300 MHz, CDCl$_3$) δ 1.87-1.90 (m, 1H), 2.20-2.25 (m, 1H), 2.74-2.98 (m, 5H), 3.77 (s, 3H), 6.63 (s, 1H), 6.68-6.72 (dd, J=2.7, 8.4 Hz, 1H), 7.0-7.03 (d, J=8.4 Hz, 1H).

2(−)-6-Methoxy-1,2,3,4-tetrahydronaphthalene-2-carboxylic acid. A 30% solution of hydrogen peroxide (3.3 mmol, 0.11 mL) in H$_2$O was added at 0° C. to a solution of (3aR-cis)-3-(6-methoxy-1,2,3,4-tetrahydronaphthalene-2(−)-carbonyl)-3,3a,8,8a-tetrahydro-2H-indeno[1,2-d]oxazol-2-one (0.20 g, 0.55 mmol) in 3:1 THF/H$_2$O (15 mL). Lithium hydroxide hydrate (0.046 g, 1.10 mmol) was then added to the solution in portions. The suspension was allowed to stir for 0.5 hours at 0° C. and then for 2 hours at room temperature. A 1.5 N solution of Na$_2$SO$_3$ (10 mL) was added in a dropwise manner and the biphasic solution was basified (pH ≈10) with saturated sodium bicarbonate solution. The solution was extracted (2×50 mL) with EtOAc, made acidic to pH 3 with HCl (10 M solution) and extracted (3×100 mL) with CH$_2$Cl$_2$. The organic extracts were combined, dried (MgSO$_4$), and concentrated under reduced pressure to provide a white solid. The solid was recrystallized from EtOAc/petroleum ether to provide 2(−)-6-methoxy-1,2,3,4-tetrahydronaphthalene-2-carboxylic acid as white needles (0.102 g, 90%). mp. 121-122° C. [a]$^{22}_D$ −56.9° (c 0.25, CHCl$_3$) $^1$H-NMR (300 MHz, CDCl$_3$) δ 1.87-1.90 (m, 1H), 2.20-2.25 (m, 1H), 2.74-2.98 (m, 5H), 3.77 (s, 3H), 6.63 (s, 1H), 6.68-6.72 (dd, J=2.7, 8.4 Hz, 1H), 7.0-7.03 (d, J=8.4 Hz, 1H).

6-Methoxy-1,2,3,4-tetrahydro-naphthalene-2(+)-carboxylic acid{1-[4-(3-hydroxyphenyl)-(3R)-(4R)-trans-dimethyl-piperidinylmethyl]-(2S)-methylpropyl}-amide. 2(+)-6-Methoxy-1,2,3,4-tetrahydronaphthalene-2-carboxylic acid (0.22 g, 1.07 mmol) was added under N$_2$ to a solution of BOP (0.47 g, 1.07 mmol), TEA (0.23 g, 2.35 mmol) and N-[(2'S)-Amino-3'-methylbutyl]-(3R,4R)-trans-dimethyl-4-(3-hydroxyphenyl)piperidine (0.31 g, 1.07 mmol) in anhydrous THF (50 mL). The solution was allowed to stir at room temperature for 6 h and sat. NaHCO$_3$ solution (100 mL) was added. The biphasic mixture was extracted with EtOAc (3×100 mL). The organic extracts were combined, dried (MgSO$_4$), and concentrated under reduced pressure to provide an oil. The oil was purified using medium pressure column chromatography on silica (CHCl$_3$/MeOH/NH$_4$OH, 9/0.8/0.2) to provide 6-methoxy-1,2,3,4-tetrahydro-naphthalene-2(+)-carboxylic acid{1-[4-(3-hydroxyphenyl)-(3R)-(4R)-trans-dimethyl-piperidinylmethyl]-(2S)-methylpropyl}-amide as a colorless oil (0.39 g, 77%). $^1$H NMR (300 MHz, CDCl$_3$) δ ppm 0.72 (d, J=6.78 Hz, 3H), 0.82-0.96 (m, 6H), 1.26 (s, 3H), 1.55 (d, J=12.43 Hz, 1H), 1.78-2.07 (m, 4H), 2.18-2.88 (m, 12H), 3.73 (s, 3H), 4.00-4.16 (m, 1 H), 6.05 (d, J=7.54 Hz, 1H), 6.57 (d, J=2.64 Hz, 1H), 6.62-6.77 (m, 3H), 6.84 (m, 1H), 6.93 (d, J=8.67 Hz, 1 H), 7.11 (t, J=7.91 Hz, 1H).

6-Hydroxy-1,2,3,4-tetrahydro-naphthalene-2(+)-carboxylic acid{1-[4-(3-hydroxyphenyl)-(3R)-(4R)-trans-dimethyl-piperidinylmethyl]-(2S)-methylpropyl}-amide Hydrochloride. A 1.0 M solution of BBr$_3$ (8.2 mL. 8.2 mmol) in CH$_2$Cl$_2$ was added at −78° C. under N$_2$ to 6-methoxy-1,2,3,4-tetrahydro-naphthalene-2(+)-carboxylic acid{1-[4-(3-hydroxyphenyl)-(3R)-(4R)-trans-dimethyl-piperidinylmethyl]-(2S)-methylpropyl}-amide (0.39 g, 0.82 mmol) in CH$_2$Cl$_2$ (25 mL). The dark brown solution was allowed to stir at −78° C. for 0.5 h and allowed to warm to room temperature. A saturated solution of NaHCO$_3$ (50 mL) was cautiously added and the biphasic mixture was extracted with EtOAc (3×100 mL). The organic extracts were combined, dried (MgSO$_4$) and concentrated under reduced pressure to provide a brown oil. The oil was purified using medium pressure column chromatography on silica (CHCl$_3$/MeOH/NH$_4$OH, 8/1.8/0.2) to provide a colorless oil (0.30 g, 77%). The hydrochloride salt was prepared by adding a 1.0 M soln of HCl in Et$_2$O to 6-hydroxy-1,2,3,4-tetrahydro-naphthalene-2(+)-carboxylic acid{1-[4-(3-hydroxyphenyl)-(3R)-(4R)-trans-dimethyl-piperidinylmethyl]-(2S)-methylpropyl}-amide in MeOH. The solution was concentrated under reduced pressure and recrystallized from EtOH/Et$_2$O to provide 6-hydroxy-1,2,3,4-tetrahydro-naphthalene-2(+)-carboxylic acid{1-[4-(3-hydroxyphenyl)-(3R)-(4R)-trans-dimethyl-piperidinylmethyl]-(2S)-methylpropyl}-amide hydrochloride as white plates. mp 189-191° C. $^1$H NMR Free Base (300 MHz, CD$_3$OD) δ ppm 0.74 (d, J=6.78 Hz, 3H), 0.90 (d, J=6.78 Hz, 3H), 0.93 (d, J=6.78 Hz, 3H), 1.27 (s, 3H), 1.55 (d, J=12.81 Hz, 1 H), 1.68-1.89 (m, 2H), 1.95 (m, 2H), 2.36-2.81 (m, 12H), 4.02 (ddd, J=9.61, 5.09, 4.90 Hz, 1H), 6.50 (d, J=2.26 Hz, 1H), 6.57 (ddd, J=15.26, 8.10, 2.26 Hz, 2H), 6.70-6.80 (m, 2 H), 6.85 (d, J=8.29 Hz, 1H), 7.10 (t, J=8.10 Hz, 1H), 7.81 (br. s., 1H). Elemental Anal for C$_{29}$H$_{41}$N$_2$ClO$_3$.0.75H$_2$O Calcd. C, 67.68; H, 8.32; N, 5.44. Found. C, 67.55; H, 8.38; N, 5.31.

6-Methoxy-1,2,3,4-tetrahydro-naphthalene-2(−)-carboxylic acid{1-[4-(3-hydroxyphenyl)-(3R)-(4R)-trans-dimethyl-piperidinylmethyl]-(2S)-methylpropyl}-amide. 2(−)-6-Methoxy-1,2,3,4-tetrahydronaphthalene-2-carboxylic acid (0.31 g, 1.48 mmol) was added under $N_2$ to a solution of BOP (0.65 g, 1.48 mmol), TEA (0.33 g, 3.26 mmol) and N-[(2'S)-Amino-3'-methylbutyl]-(3R,4R)-trans-dimethyl-4-(3-hydroxyphenyl)piperidine (0.43 g, 1.48 mmol) in anhydrous THF (65 mL). The solution was allowed to stir at room temperature for 6 h and sat. $NaHCO_3$ solution (100 mL) was added. The biphasic mixture was extracted with EtOAc (3×100 mL). The organic extracts were combined, dried ($MgSO_4$), and concentrated under reduced pressure to provide an oil. The oil was purified using medium pressure column chromatography on silica ($CHCl_3$/MeOH/$NH_4OH$, 9/0.8/0.2) to provide 6-methoxy-1,2,3,4-tetrahydro-naphthalene-2(−)-carboxylic acid{1-[4-(3-hydroxyphenyl)-(3R)-(4R)-trans-dimethyl-piperidinylmethyl]-(2S)-methylpropyl}-amide as a colorless oil (0.70 g, 98%). $^1$H NMR (300 MHz, $CDCl_3$) δ ppm 0.66-0.78 (d, J=6.9 Hz, 3H), 0.83-0.97 (m, 6H), 1.25 (s, 3H), 1.53 (d, J=12.43 Hz, 1H), 1.78-2.10 (m, 4H), 2.20-2.97 (m, 12H), 3.73 (s, 3H), 4.03 (m, 1H), 6.03 (d, J=7.54 Hz, 1 H), 6.57 (d, J=2.26 Hz, 1H), 6.61-6.75 (m, 3H), 6.82 (m, 1H), 6.90 (d, J=8.29 Hz, 1H), 7.10 (t, J=7.72 Hz, 1H).

6-Hydroxy-1,2,3,4-tetrahydro-naphthalene-2(−)-carboxylic acid{1-[4-(3-hydroxyphenyl)-(3R)-(4R)-trans-dimethyl-piperidinylmethyl]-(2S)-methylpropyl}-amide Hydrochloride. A 1.0 M solution of $BBr_3$ (8.2 mL. 8.2 mmol) in $CH_2Cl_2$ was added at −78° C. under $N_2$ to 6-methoxy-1,2,3,4-tetrahydro-naphthalene-2(−)-carboxylic acid{1-[4-(3-hydroxyphenyl)-(3R)-(4R)-trans-dimethyl-piperidinylmethyl]-(2S)-methylpropyl}-amide (0.70 g, 1.45 mmol) in $CH_2Cl_2$ (50 mL). The dark brown solution was allowed to stir at −78° C. for 0.5 h and allowed to warm to room temperature. A saturated solution of $NaHCO_3$ (100 mL) was cautiously added and the biphasic mixture was extracted with EtOAC (3×150 mL). The organic extracts were combined, dried ($MgSO_4$) and concentrated under reduced pressure to provide a brown oil. The oil was purified using medium pressure column chromatography on silica ($CHCl_3$/MeOH/$NH_4OH$, 8/1.8/0.2) to provide a colorless oil (0.57 g, 83%). The hydrochloride salt was prepared by adding a 1.0 M soln of HCl in $Et_2O$ to 6-hydroxy-1,2,3,4-tetrahydro-naphthalene-2(−)-carboxylic acid{1-[4-(3-hydroxyphenyl)-(3R)-(4R)-trans-dimethyl-piperidinylmethyl]-(2S)-methylpropyl}-amide in MeOH. The solution was concentrated under reduced pressure and recrystallized from EtOH/$Et_2O$ to provide 6-hydroxy-1,2,3,4-tetrahydro-naphthalene-2(−)-carboxylic acid{1-[4-(3-hydroxyphenyl)-(3R)-(4R)-trans-dimethyl-piperidinylmethyl]-(2S)-methylpropyl}-amide hydrochloride as tan cubes. mp 193-195° C. $^1$H NMR (500 MHz, $CD_3OD$) δ ppm 0.76 (d, J=7.32 Hz, 3 H), 0.91 (d, J=6.84 Hz, 3H), 0.95 (d, J=6.84 Hz, 3H), 1.27-1.30 (s, 3H), 1.57 (d, J=11.23 Hz, 1H), 1.75-1.86 (m, 2H), 1.95-2.03 (m, 2H), 2.29 (td, J=12.57, 4.15 Hz, 1H), 2.34-2.41 (m, 1H), 2.42-2.87 (m, 10H), 4.02 (dt, J=9.77, 4.88 Hz, 1H), 6.49 (m, 1H), 6.52 (dd, J=8.30, 2.44 Hz, 1H), 6.58 (dd, J=7.81, 1.95 Hz, 1H), 6.74 (m, 1H), 6.77 (d, J=7.81 Hz, 1H), 6.82 (d, J=8.30 Hz, 1H), 7.10 (t, J=8.06 Hz, 1H). Elemental Anal for $C_{29}H_{41}N_2ClO_3 \cdot 1.5H_2O$ Calcd. C, 65.95; H, 8.40; N, 5.30. Found. C, 65.71; H, 8.11; N, 5.21.

Synthesis of 14 and 15 (Q=S)

7-Methoxy-isothiochroman-4-one-3-carboxylic acid methyl ester. A 2.0 M solution of LDA in heptane/THF/ethylbenzene (1.61 mL, 3.21 mmol) was added in a dropwise manner to a solution of 7-methoxy-isothiochroman-4-one (0.50 g, 2.57 mmol) in THF (50 mL) at −78° C. under $N_2$. After 30 min at −78° C. HMPA (0.46 g, 2.57 mmol) and methyl cyanoformate (0.27 g, 3.21 mmol) were added and the yellow solution was allowed to stir at −78° C. for 30 min. The solution was then allowed to warm to room temperature and a saturated solution of $NH_4Cl$ (100 mL) was added. The slurry was extracted with EtOAc (3×75 mL) and the organic extracts were combined, dried ($MgSO_4$) and concentrated under reduced pressure to provide a bright yellow oil. The oil was purified on silica using medium pressure chromatography (9:1 petroleum ether/EtOAc) to provide 7-methoxy-isothiochroman-4-one-3-carboxylic acid methyl ester as a bright yellow oil (0.51 g, 78%). $^1$H-NMR (300 MHz, $CDCl_3$) δ 3.73 (s, 2H), 3.83 (s, 3H), 3.85 (s, 3H), 6.67 (d, J=3 Hz, 1H), 6.45 (dd, J=3, 8.7 Hz, 1H), 7.80 (d, J=8.7 Hz, 1H), 12.52 (s, 1H).

7-Methoxy-isothiochroman-3-carboxylic acid methyl ester. Triethylsilane (8.08 mmol, 0.94 g) was added to a solution of 7-methoxy-isothiochroman-4-one-3-carboxylic acid methyl ester (0.51 g, 2.02 mmol) in trifluoroacetic acid (15 mL) at room temperature under $N_2$. The reaction was allowed to stir at room temperature for 2 h and was concentrated under reduced pressure. The resulting oil was dissolved in EtOAc (100 mL) and washed with sat. $NaHCO_3$ (3×75 mL). The organic extracts were combined, dried ($MgSO_4$) and concentrated to provide an oil. The oil was purified on silica using medium pressure chromatography (9:1 petroleum ether/EtOAc) to provide 7-methoxy-isothiochroman-3-carboxylic acid methyl ester (0.34 g, 70%) as a pale yellow oil. $^1$H-NMR (300 MHz, $CDCl_3$) δ 3.14 (m, 2H), 3.58-3.63 (d, J=15 Hz, 1H), 3.73-3.86 (m, 8H), 6.70 (d, J=3 Hz, 1H), 6.75 (dd, J=3, 9 Hz, 1H), 7.10 (d, J=9 Hz, 1H).

7-Methoxy-isothiochroman-3-carboxylic acid. Potassium hydroxide (0.80 g, 14.3 mmol) was added to a solution of 7-methoxy-isothiochroman-3-carboxylic acid methyl ester (0.34 g, 1.43 mmol) in MeOH (50 mL). The solution was heated at 60° C. for 2 h, cooled to room temperature, and diluted with $H_2O$ (100 mL). The solution was made acidic with 6 M HCl and extracted with EtOAc (3×100 mL). The organic extracts were combined, dried ($MgSO_4$) and concentrated to give 7-methoxy-isothiochroman-3-carboxylic acid (0.28 g, 88%) as a pale yellow solid. The solid was used in the next step without further purification.

7-Methoxy-isothiochroman-3-carbonyl chloride. A 2.0 M solution of oxalyl chloride (3.57 mL, 7.14 mmol) in $CH_2Cl_2$ was added under $N_2$ to a solution of 7-methoxy-isothiochroman-3-carboxylic acid (0.80 g, 3.57 mmol) and a drop of DMF in $CH_2Cl_2$ (100 mL). The solution was allowed to stir at room temperature for 3 h and was concentrated under reduced pressure to provide 7-methoxy-isothiochroman-3-carbonyl chloride as a tan oil. The acid halide was used in the next step without further purification.

(3aR-cis)-3-(7-Methoxy-isothiochroman-3(+ and −)-carbonyl)-3,3a,8,8a-tetrahydro-2H-indeno[1,2-d]oxazol-2-one. A 0.50 M solution of ethyl lithium (8.6 mL, 4.28 mmol) in benzene/cyclohexane 90:10 was added to a solution of (3aR-cis)-3,3a,8,8a-tetrahydro-2H-indeno[1,2-d]oxazol-2-one (0.75 g, 4.28 mmol) in THF (100 mL) at 0° C. under $N_2$. The suspension was allowed to stir at 0° C. for 0.5 h and was then cooled to −78° C. A solution of 7-methoxy-isothiochroman-3-carbonyl chloride (0.86 g, 3.57 mmol) in THF (10 mL) was then added in a dropwise manner to the −78° C. slurry. The resulting slurry was allowed to warm to room temperature over 2 hours and water (150 mL) was then added. The suspension was extracted with $CH_2Cl_2$ (3×150 mL). The organic extracts were combined, dried ($MgSO_4$), and concentrated under reduced pressure to provide a tan solid. The solid was purified on silica using medium pressure column chromatography (60:40 petroleum ether/Et$_2$O) to provide each of the diastereomers in 62% (+ isomer) and 37% (− isomer) theoretical yield. The yield improves with additional chromatography. The less polar spot was later identified as the (+) isomer while the more polar was (−).

Analysis for: (3a(R)-cis)-3-(7-Methoxy-isothiochroman-3 (+)-carbonyl)-3,3a,8,8a-tetrahydro-2H-indeno[1,2-d]oxazol-2-one. The solid was recrystallized from EtOAc/petroleum ether to provide a white solid (0.42 g, 62%). mp. 146-147° C. $^1$H-NMR (300 MHz, CDCl$_3$) δ 3.09-3.16 (dd, J=6, 15.6 Hz, 1H), 3.20-3.28 (dd, J=7.2, 15.3 Hz, 1H), 3.38-3.39 (d, J=3.6 Hz, 2H), 3.59-3.64 (d, J=15 Hz, 1H), 3.79 (s, 3H), 3.85-3.90 (d, J=15 Hz, 1H), 4.97-5.01 (m, 1H), 5.30-5.35 (m, 1H), 5.92-5.95 (d, J=7 Hz, 1H), 6.71-6.72 (d, J=2.7 Hz, 1H), 6.75-6.79 (dd, J=2.4, 8.4 Hz, 1H), 7.06-7.09 (d, J=8.4 Hz, 1H), 7.23-7.38 (m, 3H), 7.58-7.61 (d, J=7.5 Hz, 1H).

Analysis for: (3aR-cis)-3-(7-Methoxy-isothiochroman-3 (−)-carbonyl)-3,3a,8,8a-tetrahydro-2H-indeno[1,2-d]oxazol-2-one. The solid was recrystallized from ethyl acetate/petroleum ether to provide a white solid (0.25 g, 37%). mp. 176-178° C. $^1$H-NMR (300 MHz, CDCl$_3$) δ 3.14-3.19 (dd, J=6, 12.6 Hz, 1H), 3.24-3.29 (dd, J=7.5, 15.3 Hz, 1H), 3.39-3.40 (d, J=3.6 Hz, 2H), 3.48-3.55 (d, J=15 Hz, 1H), 3.79 (s, 3H), 3.83-3.88 (d, J=15 Hz, 1H), 4.91-4.95 (m, 1H), 5.29-5.33 (m, 1H), 5.96-5.99 (d, J=7 Hz, 1H), 6.71-6.72 (d, J=2.7 Hz, 1H), 6.76-6.80 (dd, J=2.4, 8.4 Hz, 1H), 7.10-7.12 (d, J=8.4 Hz, 1H), 7.26-7.38 (m, 3H), 7.58-7.61 (d, J=7.5 Hz, 1H).

3(+)-7-Methoxy-isothiochroman-3-carboxylic acid. Lithium hydroxide hydrate (0.093 g, 2.2 mmol) was added at 0° C. to a solution of (3aR-cis)-3-(7-methoxy-isothiochroman-3(+)-carbonyl)-3,3a,8,8a-tetrahydro-2H-indeno[1,2-d] oxazol-2-one (0.42 g, 1.10 mmol) in 3:1 THF/H$_2$O (25 mL). The suspension was allowed to stir for 0.5 hours at 0° C. The reaction was made basic (pH ≈10) with saturated sodium bicarbonate solution and the solution was extracted with Et$_2$O (1×100 mL), made acidic to pH 3 with HCl (6 M solution) and extracted with EtOAc (3×10 mL). The organic extracts were combined, dried (MgSO$_4$), and concentrated under reduced pressure to provide a white solid (0.25 g, 100%). The solid was recrystallized from toluene/petroleum ether to provide 3(+)-7-methoxy-isothiochroman-3-carboxylic acid as tan cubes. mp. 117-118-C. [α]$^{22}_D$ +98.30 (c 0.24, MeOH) $^1$H-NMR (300 MHz, CD$_3$OD) δ 2.97-3.01 (dd, J=9.3, 15 Hz, 1H), 3.10-3.17 (dd, J=5.1, 15.3, 1H), 3.63-3.88 (m, 6H), 6.75-6.77 (m, 2H), 7.08-7.11 (d, J=8.2 Hz, 1H).

3(−)-7-Methoxy-isothiochroman-3-carboxylic acid. Lithium hydroxide hydrate (0.055 g, 1.32 mmol) was added at 0° C. to a solution of (3aR-cis)-3-(7-methoxy-isothiochroman-3(−)-carbonyl)-3,3a,8,8a-tetrahydro-2H-indeno[1,2-d] oxazol-2-one (0.25 g, 0.66 mmol) in 3:1 THF/H$_2$O (15 mL). The suspension was allowed to stir for 0.5 hours at 0° C. The reaction was made basic (pH ≈10) with saturated sodium bicarbonate solution and the solution was extracted with Et$_2$O (1×100 mL), made acidic to pH 3 with HCl (6 M solution) and extracted with EtOAc (3×100 mL). The organic extracts were combined, dried (MgSO$_4$), and concentrated under reduced pressure to provide a white solid (0.136 g, 92%). The solid was recrystallized from toluene/petroleum ether to provide 3(−)-7-methoxy-isothiochroman-3-carboxylic acid as pale yellow needles. mp. 121-122° C. [α]$^{22}_D$ −100.80 (c 0.26, MeOH) $^1$H-NMR (300 MHz, CD$_3$OD) δ 2.97-3.01 (dd, J=9.3, 15 Hz, 1H), 3.10-3.17 (dd, J=5.1, 15.3, 1H), 3.63-3.88 (m, 6H), 6.75-6.77 (m, 2H), 7.08-7.11 (d, J=8.2 Hz, 1H).

7-Methoxy-isothiochroman-3(+)-carboxylic acid{1-[4-(3-hydroxyphenyl)-(3R)-(4R)-trans-dimethyl-piperidinylmethyl]-(2S)-methylpropyl}-amide. 3(+)-7-Methoxy-isothiochroman-3-carboxylic acid (0.25 g, 1.12 mmol) was added under N$_2$ to a solution of BOP (0.50 g, 1.12 mmol), TEA (0.23 g, 2.24 mmol) and N-[(2'S)-Amino-3'-methylbutyl]-(3R, 4R)-trans-dimethyl-4-(3-hydroxyphenyl)piperidine (0.33 g, 1.12 mmol) in anhydrous THF (50 mL). The solution was allowed to stir at room temperature for 6 h and sat. NaHCO$_3$ solution (100 mL) was added. The biphasic mixture was extracted with EtOAc (3×100 mL). The organic extracts were combined, dried (MgSO$_4$), and concentrated under reduced pressure to provide an oil. The oil was purified using medium pressure column chromatography on silica (CHCl$_3$/MeOH/ NH$_4$OH, 9/0.8/0.2) to provide 7-methoxy-isothiochroman-3 (+)-carboxylic acid{1-[4-(3-hydroxyphenyl)-(3R)-(4R)-trans-dimethyl-piperidinylmethyl]-(2S)-methylpropyl}-amide as a pale yellow semisolid (0.45 g, 81%). $^1$H NMR (300 MHz, CDCl$_3$) δ 0.49-0.55 (m, 6H), 0.67-0.69 (d, J=6 Hz, 3H), 1.24 (s, 3H), 1.48-1.52 (d, J=12 Hz, 1H), 1.62-1.70 (m, 1H), 1.86-1.88 (m, 1H), 2.14-2.52 (m, 6H), 2.61-2.71 (m, 2H), 2.89-2.95 (dd, J=5.1, 14.4 Hz, 1H), 3.31-3.38 (dd, J=5.4, 14.4 Hz, 1H), 3.57-3.62 (d, J=13.8 Hz, 1H), 3.65-3.69 (d, J=13.8 Hz, 1H), 3.74 (s, 3H), 3.84-3.87 (m, 1H), 6.70-6.72 (m, 3H), 6.84-6.89 (m, 2H), 7.03-7.12 (m, 2H).

7-Hydroxy-isothiochroman-3(+)-carboxylic acid{1-[4-(3-hydroxyphenyl)-(3R)-(4R)-trans-dimethyl-piperidinylmethyl]-(2S)-methylpropyl}-amide. A 1.0 M solution of BBr$_3$ (9.1 mL. 9.1 mmol) in CH$_2$Cl$_2$ was added at −78° C. under N$_2$ to 7-methoxy-isothiochroman-3(+)-carboxylic acid{1-[4-(3-hydroxyphenyl)-(3R)-(4R)-trans-dimethyl-piperidinylmethyl]-(2S)-methylpropyl}-amide (0.45 g, 0.91 mmol) in CH$_2$Cl$_2$ (100 mL). The dark brown solution was allowed to stir at −78° C. for 0.5 h and allowed to warm to 0° C. for 2 h. A saturated solution of NaHCO$_3$ (100 mL) was cautiously added and the biphasic mixture was extracted with EtOAC (3×150 mL). The organic extracts were combined, dried (MgSO$_4$) and concentrated under reduced pressure to provide a brown oil. The oil was purified using medium pressure column chromatography on silica (CHCl$_3$/MeOH/NH$_4$OH, 8/1.8/0.2) to provide a tan semisolid (0.43 g, 98%). The solid was recrystallized from acetone/petroleum ether to afford 7-hydroxy-isothiochroman-3(+)-carboxylic acid{1-[4-(3-hydroxyphenyl)-(3R)-(4R)-trans-dimethyl-piperidinylmethyl]-(2S)-methylpropyl}-amide as white needles. mp 133-135° C. $^1$H NMR (300 MHz, CD$_3$OD) δ 0.69-0.74 (m, 9H), 0.89-0.98 (m, 1H), 1.28 (s, 3H), 1.52-1.59 (d, J=12.9 Hz, 1H), 1.64-1.68 (m, 1H), 1.94-1.96 (m, 1H), 2.17-2.47 (m, 4H), 2.58-2.62 (d, J=11.3 Hz, 1H), 2.72-2.75 (d, J=11.3 Hz, 1H), 2.89-2.96 (dd, J=5.3, 15 Hz, 1H), 3.11-3.18 (dd, J=7.54, 14.3 Hz, 1H), 3.62-3.77 (m, 3H), 3.83-3.90 (m, 1H), 6.54-6.65 (m, 3H), 6.71-6.76 (m, 2H), 6.91-6.94 (d, J=8.2 Hz, 1H), 7.06-7.11 (t, J=7.9 Hz, 1H).

7-Methoxy-isothiochroman-3(−)-carboxylic acid{1-[4-(3-hydroxyphenyl)-(3R)-(4R)-trans-dimethyl-piperidinylmethyl]-(2S)-methylpropyl}-amide. 3(−)-7-Methoxy-isothiochroman-3-carboxylic acid (0.24 g, 1.07 mmol) was added under N$_2$ to a solution of BOP (0.47 g, 1.07 mmol), TEA (0.21 g, 2.14 mmol) and N-[(2'S)-amino-3'-methylbutyl]-(3R,4R)-trans-dimethyl-4-(3-hydroxyphenyl)piperidine (0.31 g, 1.07 mmol) in anhydrous THF (50 mL). The solution was allowed to stir at room temperature for 6 h and sat. NaHCO$_3$ solution (100 mL) was added. The biphasic mixture was extracted with EtOAc (3×100 mL). The organic extracts were combined, dried (MgSO$_4$), and concentrated under reduced pressure to provide an oil. The oil was purified using medium pressure column chromatography on silica (CHCl$_3$/MeOH/ NH$_4$OH, 9/0.8/0.2) to provide 7-methoxy-isothiochroman-3 (−)-carboxylic acid{1-[4-(3-hydroxyphenyl)-(3R)-(4R)-trans-dimethyl-piperidinylmethyl]-(2S)-methylpropyl}- amide as a pale yellow semisolid (0.44 g, 84%). $^1$H NMR (300 MHz, CDCl$_3$) δ 0.65-0.68 (d, J=6.9 Hz, 3H), 0.77-0.79 (d, J=4.2 Hz, 3H), 0.84-0.86 (d, J=6.6 Hz, 3H), 1.27 (s, 3H), 1.47-1.51 (d, J=12.3 Hz, 1H), 1.80-2.70 (m, 11H) 3.03-3.09 (dd, J=5.4, 14.7 Hz, 1H), 3.17-3.24 (dd, J=6.3, 14.4 Hz, 1H), 3.60-3.65 (d, J=14.1 Hz, 1H), 3.67-3.72 (d, J=14.1 Hz, 1H), 3.77 (s, 3H), 3.83-3.87 (m, 1H), 6.59-6.83 (m, 5H), 7.05-7.16 (m, 2H).

7-Hydroxy-isothiochroman-3(−)-carboxylic acid{1-[4-(3-hydroxyphenyl)-(3R)-(4R)-trans-dimethyl-piperidinylmethyl]-(2S)-methylpropyl}-amide Hydrochloride. A 1.0 M solution of BBr$_3$ (9.0 mL. 9.0 mmol) in CH$_2$Cl$_2$ was added at −78° C. under N$_2$ to 7-methoxy-isothiochroman-3(−)-carboxylic acid{1-[4-(3-hydroxyphenyl)-(3R)-(4R)-trans-dimethyl-piperidinylmethyl]-(2S)-methylpropyl}-amide (0.44 g, 0.90 mmol) in CH$_2$Cl$_2$ (100 mL). The dark brown solution was allowed to stir at −78° C. for 0.5 h and allowed to warm to 0° C. for 2 h. A saturated solution of NaHCO$_3$ (100 mL) was cautiously added and the biphasic mixture was extracted with EtOAC (3×150 mL). The organic extracts were combined, dried (MgSO$_4$) and concentrated under reduced pressure to provide a brown oil. The oil was purified using medium pressure column chromatography on silica (CHCl$_3$/MeOH/NH$_4$OH, 8/1.8/0.2) to provide a tan semisolid (0.40 g, 93%). The hydrochloride salt was prepared by adding a 1.0 M soln of HCl in Et$_2$O to 7-hydroxy-isothiochroman-3 (−)-carboxylic acid{1-[4-(3-hydroxyphenyl)-(3R)-(4R)-trans-dimethyl-piperidinylmethyl]-(2S)-methylpropyl}-amide in MeOH. The solution was concentrated under reduced pressure and recrystallized from EtOH/Et$_2$O to provide 7-hydroxy-isothiochroman-3(−)-carboxylic acid{1-[4-(3-hydroxyphenyl)-(3R)-(4R)-trans-dimethyl-piperidinylmethyl]-(2S)-methylpropyl}-amide hydrochloride as white cubes. mp 224-227° C., (191-194° C. softens); $^1$H NMR Free Base (300 MHz, CD$_3$OD) δ 0.71-0.74 (d, J=6.8 Hz, 3H), 0.83-0.85 (d, J=6.8 Hz, 3H), 0.88-0.90 (d, J=6.8 Hz, 3H), 1.06-1.13 (m, 1H), 1.26 (s, 3H), 1.50-1.54 (d, J=12.4 Hz, 1H), 1.79-1.94 (m, 2H), 2.15-2.39 (m, 4H), 2.48 (brs, 1H), 2.71-2.75 (d, J=11 Hz, 1H), 2.97-3.10 (m, 2H), 3.58-3.78 (m, 3H), 3.85-3.91 (m, 1H), 6.57-6.60 (d, J=7.9 Hz, 1H), 6.63 (m, 2H), 6.73 (m, 2H), 6.95-6.98 (d, J=8.2 Hz, 1H), 7.06-7.12 (t, J=7.9 Hz, 1H).

Biological

In Vitro

Measures of opioid receptor antagonism were obtained by monitoring selected test compounds ability to inhibit stimulation of [$^{35}$S]GTPγS binding produced by the selective agonists (D-Ala$^2$,MePhe$^4$,Gly-ol$^5$)enkephalin (DAMGO, mu receptor), cyclo[D-Pen$^2$,D-Pen$^5$]enkephalin (DPDPE, delta) and 5,7,8-(−)-N-methyl-N-[7-(1-pyrrolidinyl)-1-oxaspiro[4,5]dec-8-yl]benzeneacetamide (U69,593, kappa) in cloned human receptors, Table 1.

TABLE 1

Inhibition of Agonist Stimulated [$^{35}$S]GTPγS Binding by Compounds in Cloned Human μ, δ, and κ Opioid Receptors

| RTI-5989- | μ, DAMGO $K_e$ (nM) | δ, DPDPE $K_e$ (nM) | κ, U69,593 $K_e$ (nM) | μ/κ | δ/κ |
|---|---|---|---|---|---|
| 160 | 6.67 ± 1.20 | 44.8 ± 7.7 | 0.18 ± 0.03 | 37 | 248 |
| 161 | 11.2 ± 2.4 | 205 ± 59 | 1.37 ± 0.36 | 8.2 | 150 |

In Vivo

These in vivo experiments were used to determine the ability of a putative kappa antagonist to inhibit kappa agonist-induced increases in urine output. The experiments were designed to assess both the acute and long-term affects of the test compound. During the acute phase, the dose of test compound was immediately followed by the administration of the kappa agonist, U50,488, and urine output monitored every hour for five hours. To evaluate the long-term effects of the test compound, the same rats were given weekly challenge doses of agonist for three weeks and urine output monitored.

Adult male Sprague-Dawley rats (Charles River Laboratory, Raleigh, N.C.) were used for these studies. The test compound and U50,488 doses were prepared fresh in distilled deionized water (vehicle) and administered (1 mL/kg body weight) via subcutaneous injection. Six groups of four rats were used to evaluate each test compound: vehicle control (Group 1), agonist control (10 mg/kg, Group 2), test compound at 3, 10 or 30 mg/kg followed by agonist (10 mg/kg, Groups 3-5) and a test compound control (30 mg/kg, Group 6). Each rat was weighed prior to dosing. One rat from each group was dosed in succession and the pattern repeated to distribute any effects of time of day across all groups. After dosing, each rat was placed into a metabolic chamber and urine output collected hourly for five hours. Urine output for each collection period was calculated as (urine+collection tube weight)−collection tube tare weight. The effect of test compound on total urine output was assessed using Analysis of Variance with repeated measures (subject within Group) using factors of Group and Time and their interaction, or one-way ANOVA, where appropriate. A univariate ANOVA was run only if a significant effect was observed following the multivariate ANOVA. Significance was assumed at p<0.05 for the individual factors and p<0.1 for their interaction.

Results and Discussion

Compounds RTI-5989-160 and RTI-5989-161 (which correspond to compounds of Formulae 14 and 15, although the exact correspondence has not yet been determined, Q=CH$_2$) show high potency for the kappa opioid receptor in the [$^{35}$S] GTPγS in vitro functional assay. Note that RTI-5989-160 with a K$_e$ value of 0.18 has subnanomolar potency, and since its K$_e$s at the μ and δ opioid receptors are 6.67 and 44.8 nM, it is highly selective for the kappa opioid receptor.

Figure 5A:
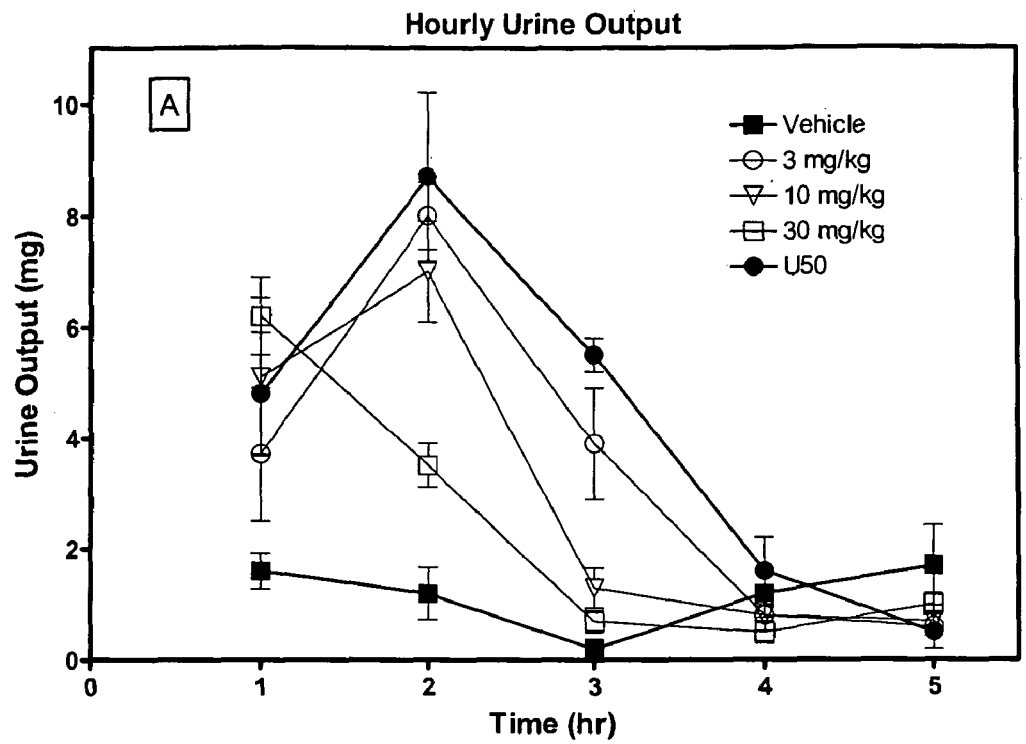
FIG. 5: graphical representation of effect of compound 160 (one of compounds 14 or 15) on U50,488-stimulated urine output.
Figure 5B:
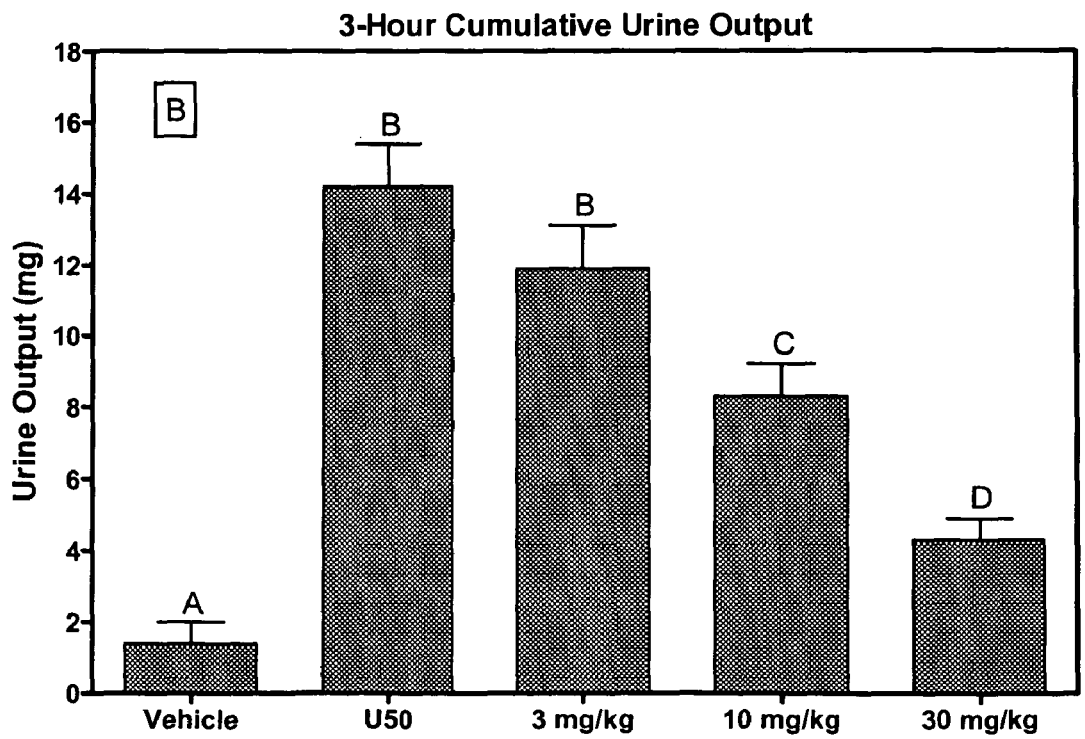
Figure 6:
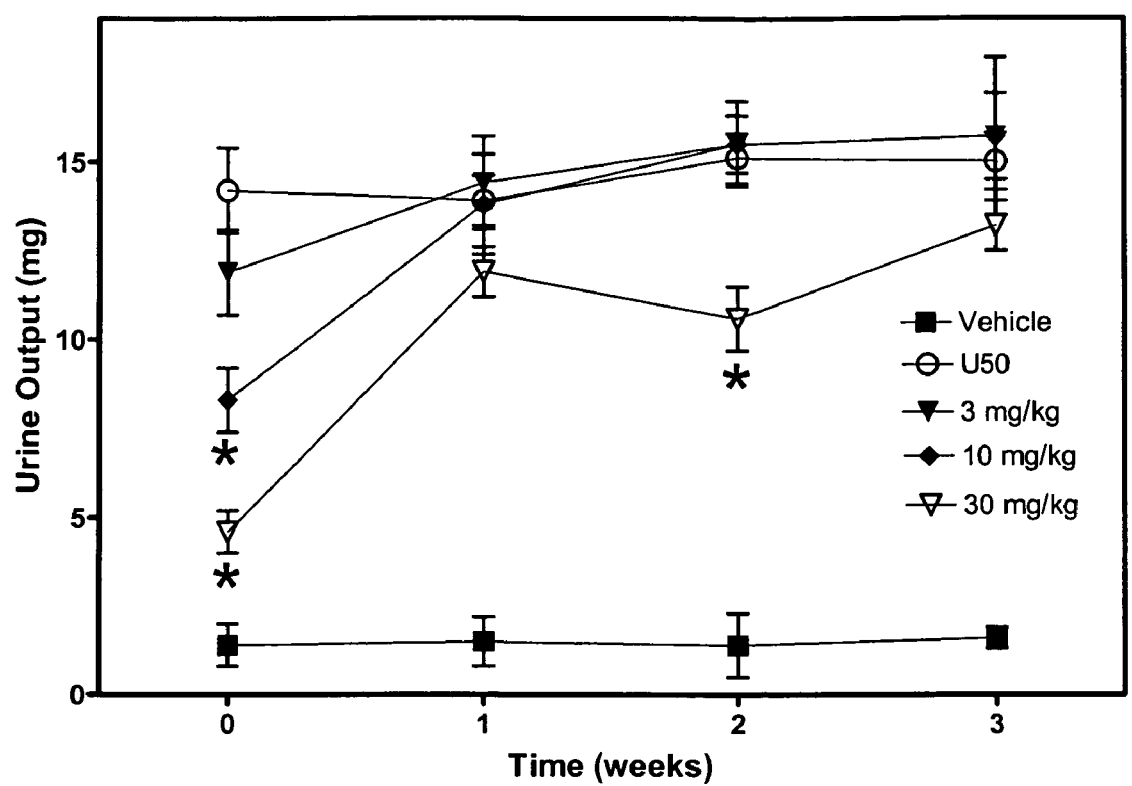
FIG. 6: graphical representation of long-term effect of compound 160 (one of compounds 14 or 15) on U50,488 urine output.

FIG. 5 shows the effect of compound 160 on U50,488-stimulated urine output. The results represent the mean±SE of data collected from four rats per dose group. Panel A shows urine output for the five one-hour collection periods on the first day of dosing. Panel B shows the cumulative urine output for the first three hours. The three-hour time point was chosen because after that time, there was no longer any effect of U50, 488 to inhibit. Bars marked with different letters are significantly different from each other. On the first day of dosing, compound RTI-5989-160 caused a dose dependent decrease in U50,488-stimulated diuresis, with individual significance observed for the 10 and 30 mg/kg dose groups (FIG. 5). FIG. 6 shows the long-term effect of compound 160 on U50,488 urine output. The results represent the mean±SE of data collected from four rats per dose group. Note that urine output returns to control levels by one week after dosing, but a transient and significant decrease in agonist-stimulated urine output is observed in the 30 mg/kg dose group two weeks after antagonist dosing. In keeping with earlier work, the diuretic effect of U50,488 peaked two hours after administration, and urine output fell to vehicle control levels by four hours after dosing. Neither compound RTI-5989-160 nor RTI-5989-161 affected urine output or caused any observable toxicity at the top dose of 30 mg/kg (not shown).

CONCLUSIONS

The compounds of the present invention are potent kappa opioid receptor antagonists in an in vitro functional test. They show good selectivity relative to the mu and delta opioid receptors. Compound RTI-5989-160's ability to antagonize diuresis induced by the kappa agonist U50,488 in rats shows that these compounds are also potent kappa opioid receptor antagonists in vivo.

REFERENCES (1) Aldrich, J. V. Analgesics. In *Burger's Medicinal Chemistry and Drug Discovery*, Wolff, M. E. Eds.; John Wiley & Sons: New York, 1996; Vol. 3.

(2) Volpicelli, J. R.; Alterman, A. I.; Hayashida, M.; O'Brien, C. P. Naltrexone in the treatment of alcohol dependence. *Arch. Gen. Psychiatry* 1992, 49, 876-879.

(3) Volpicelli, J. R.; Watson, N. T.; King, A. C.; Sherman, C. E.; O'Brien, C. P. Effect of naltrexone on alcohol "high" in alcoholics. *Am. J. Psychiatry* 1995, 152, 613-615.

(4) Marki, A.; Monory, K.; Otvos, F.; Toth, G.; Krassnig, R.; Schmidhammer, H.; Traynor, J. R.; Roques, B. P.; Maldonado, R.; Borsodi, A. Mu-opioid receptor specific antagonist cyprodime: characterization by in vitro radioligand and [35S]GTPgammaS binding assays. *Eur J Pharmacol* 1999, 383(2), 209-14.

(5) Portoghese, P. S. The design of selective opioid receptor antagonists. *Il Fannaco* 1993, 48(2), 243-251.

(6) Portoghese, P. S.; Lipkowski, A. W.; Takemori, A. E. Binaltorphimine and nor-binaltorphimine, potent and selective-opioid receptor antagonists. *Life Sci.* 1987, 40(13), 1287-1292.

(7) Olmsted, S. L.; Takemori, A. E.; Portoghese, P. S. A remarkable change of opioid receptor selectivity on the attachment of a peptidomimetic address element to the antagonist, natrindole: 5'-[N$^2$-alkylamidino)methyl]naltrindole derivatives as a novel class of opiold receptor antagonists. *J. Med. Chem.* 1993, 36(1), 179-180.

(8) Jones, R. M.; Hjorth, S. A.; Schwartz, T. W.; Portoghese, P. S. Mutational evidence for a common kappa antagonist binding pocket in the wild-type kappa and mutant mu[K303E] opioid receptors. *J Med Chem* 1998, 41(25), 4911-4.

(9) Schwyzer, R. ACTH: A short introductory review. *Ann. N.Y Acad. Sci.* 1977, 247, 3-26.

(10) Trujillo, K. A.; Akil, H. Changes in prodynorphin peptide content following treatment with morphine or amphetamine: possible role in mechanisms of action of drug of abuse. *NIDA Res Monogr* 1989, 95, 550-1.

(11) Smiley, P. L.; Johnson, M.; Bush, L.; Gibb, J. W.; Hanson, G. R. Effects of cocaine on extrapyramidal and limbic dynorphin systems. *J Pharmacol Exp Ther* 1990, 253(3), 938-43.

(12) Corbett, A. D.; Paterson, S. J.; McKnight, A. T.; Magnan, J.; Kosterlitz, H. W. Dynorphin and dynorphin are ligands for the kappa-subtype of opiate receptor. *Nature* 1982, 299(5878), 79-81.

(13) Spanagel, R.; Herz, A.; Shippinberg, T. A. Opposing tonically active endogenous opioid systems modulate the mesolimbic dopaniinergic pathway. *Proc. Natl. Acad. Sci. U.S.A.* 1992, 89, 2046-2050.

(14) Spanagel, R.; Shippenberg, T. S. Modulation of morphine-induced sensitization by endogenous opioid systems in the rat. *Neurosci. Lett.* 1993, 153, 232-236.

(15) Zadina, J. E.; Hackler, L.; Ge, L.-J.; Kastin, A. J. A potent and selective endogenous agonist for the opiate receptor. *Nature* 1997, 386, 499-502.

(16) Zinunerman, D. M.; Nickander, R.; Homg, J. S.; Wong, D. T. New structural concepts for narcotic antagonists defined in a 4-phenylpiperidine series. *Nature* 1978, 275, 332-334.

(17) Zimmerman, D. M.; Smits, S.; Nickander, R. Further investigation of novel 3-methyl-4-phenylpiperidine narcotic antagonists. In *Proceedings of the 40th Annual Scientific Meeting of the Committee on Problems of Drug Dependence*, 1978, pp. 237-247.

(18) Zimmerman, D. M.; Smits, S. E.; Hynes, M. D.; Cantrell, B. E.; Reamer, M.; Nickander Structural requirements for affinity and intrinsic activity at the opiate receptor defined in 4-phenylpiperidine and related series. In *Problems of Drug Dependence* 1981, *Proceedings of the 43rd Annual Scientific Meeting of the Committee on Problems of Drug Dependence*, Inc., Harris, L. S. Eds.; 1981, pp. 112-116.

(19) Zimmerman, D. M.; Smits, S. E.; Hynes, M. D.; Cantrell, B. E.; Reamer, M.; Nickander, R. Structural requirements for affinity and intrinsic activity at the opiate receptor defined in 4-phenylpiperidine and related series. In *Problems of Drug Dependence*, 1981, *Proceedings of the 43rd Annual Scientific Meeting*, The committee on Problems of Drug Dependence, Inc., Harris, L. S. Eds.; Committee on Problems of Drug Dependence, Inc.: 1982; Vol. NIDA Research Monograph 41, pp. 112-118.

(20) Zimmerman, D. M.; Cantrell, B. E.; Swartzendruber, J. K.; Jones, N. D.; Mendelsohn, L. G.; Leander, J. D.; Nickander, R. C. Synthesis and analgesic properties of N-substituted trans-4a-aryldecahydroisoquinolines. *J. Med. Chem.* 1988, 31, 555-560.

(21) Zimmerman, D. M.; Leander, J. D.; Cantrell, B. E.; Reel, J. K.; Snoddy, J.; Mendelsohn, L. G.; Johnson, B. G.; Mitch, C. H. Structure-activity relationships of the trans-3,4-dimethyl-4-(3-hydroxyphenyl)piperidine antagonists for and opioid receptors. *J. Med. Chem.* 1993, 36(20), 2833-2841.

(22) Zimmerman, D. M.; Hermann, R. B.; Mitch, C. H.; Shaw, W. N.; Mendelsohn, L. G.; Leander, J. D. Opioid receptor antagonists: Comparison of trans-3,4-dimethyl-4-phenylpiperidines and their use in the development of a model of opioid receptors. *Pharmacol. Rev.* in press.

(23) Thomas, J. B.; Mascarella, S. W.; Rothman, R. B.; Partilla, J. S.; Xu, H.; McCullough, K. B.; Dersch, C. M.; Cantrell, B. E.; Zimmerman, D. M.; Carroll, F. I. Investigation of the N-substituent conformation governing potency and receptor subtype-selectivity in (+)-(3R,4R)-dimethyl-4-(3-hydroxyphenyl)piperidine opioid antagonists. *J. Med. Chem.* 1998, 41(11), 1980-1990.

(24) Thomas, J. B.; Fall, M. J.; Cooper, J. B.; Rothman, R. B.; Mascarella, S. W.; Xu, H.; Partilla, J. S.; Dersch, C. M.; McCullough, K. B.; Cantrell, B. E.; Zimmerman, D. M.; Carroll, F. I. Identification of opioid receptor subtype-selective N-substituent for (+)-(3R,4R)-dimethyl-4-(3-hydroxyphenyl)piperidine. *J. Med. Chem.* 1998, 41(26), 5188-5197.

(25) Werner, J. A.; Cerbone, L. R.; Frank, S. A.; Ward, J. A.; Labib, P.; Tharp-Taylor, R. W.; Ryan, C. W. Synthesis of trans-3,4-dimethyl-4-(3-hydroxyphenyl)piperidine opioid antagonists: Application of the cis-thermal elimination of carbonates to alkaloid synthesis. *J. Org. Chem.* 1996, 61, 587-597.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of binding a kappa opioid receptor in a subject having a disease state selected from the group consisting of opiate addiction, cocaine addiction, nicotine addiction and ethanol addiction, comprising:

administering to said subject a composition comprising a kappa opioid receptor antagonist and a physiologically acceptable carrier, wherein the kappa opioid receptor antagonist is a compound of formula (1):

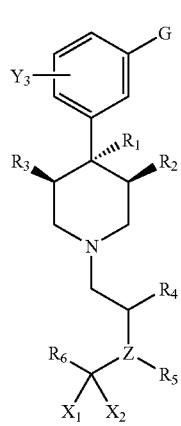

(I)

wherein G is H, OH, OCOC$_{1-8}$ alkyl, CONH$_2$, NHCHO, NH$_2$, NHSO$_2$C$_{1-8}$ alkyl, or NHCO$_2$C$_{1-8}$ alkyl;

R$_1$ is C$_{1-8}$ alkyl, or one of the following structures:

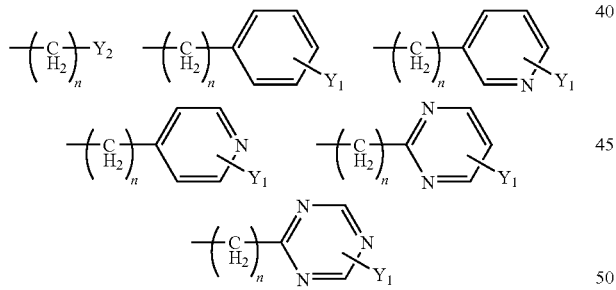

Y$_1$, is H, OH, Br, Cl, F, CN, CF$_3$, NO$_2$, N$_3$, OR$_8$, CO$_2$R$_9$, C$_{1-9}$ alkyl, NR$_{10}$R$_{11}$, NHCOR$_{12}$, NHCO$_2$R$_{12}$, CONR$_{13}$R$_{14}$, or CH$_2$(CH$_2$)$_n$Y$_2$;

Y$_2$ is H, CF$_3$, CO$_2$R$_9$, C$_{1-6}$alkyl, NR$_{10}$R$_{11}$, NHCOR$_{12}$, NHCO$_2$R$_{12}$, CONR$_{13}$R$_{14}$, CH$_2$OH, CH$_2$OR$_8$, or COCH$_2$R$_9$;

Y$_3$ is H, OH, Br, Cl, F, CN, CF$_3$, NO$_2$, N$_3$, OR$_8$, CO$_2$R$_9$, C$_{1-6}$ alkyl, NR$_{10}$R$_{11}$, NHCOR$_{12}$, NHCO$_2$R$_{12}$, CONR$_{13}$R$_{14}$, or CH$_2$(CH$_2$)$_n$Y$_2$;

R$_2$ is H, C$_{1-8}$ alkyl, C$_{3-8}$ alkenyl, C$_{3-8}$ alkynyl or CH$_2$aryl substituted by one or more groups Y$_1$;

R$_3$ is H, C$_{1-8}$ alkyl, C$_{3-8}$ alkenyl, C$_{3-8}$ alkynyl or CH$_2$aryl substituted by one or more groups Y$_1$;

wherein R$_2$ and R$_3$ may be bonded together to form a C$_{2-8}$, alkyl group;

R$_4$ is hydrogen, C$_{1-8}$ alkyl, CO$_2$C$_{1-8}$ alkylaryl substituted by one or more groups Y$_1$, CH$_2$aryl substituted by one or more groups Y$_1$ or CO$_2$C$_{1-8}$ alkyl;

Z is N, O or S; where Z is O or S, there is no R$_5$

R$_5$ is H, C$_{1-8}$ alkyl, C$_{3-8}$ alkenyl, C$_{3-8}$ alkynyl, CH$_2$CO$_2$C$_{1-8}$ alkyl, CO$_2$C$_{1-8}$ alkyl or CH$_2$aryl substituted by one or more groups Y$_1$;

n is 0, 1, 2 or 3;

R$_6$ is a group selected from the group consisting of structures (c)-(p):

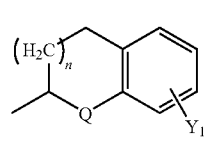
(c)

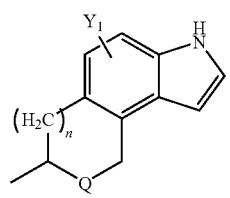
(d)

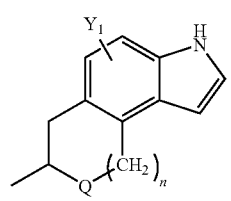
(e)

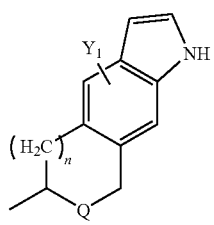
(f)

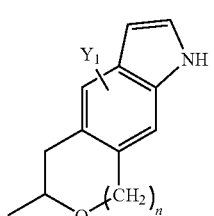
(g)

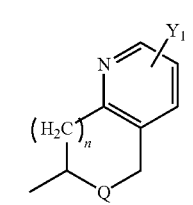
(h)

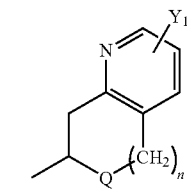
(i)

-continued

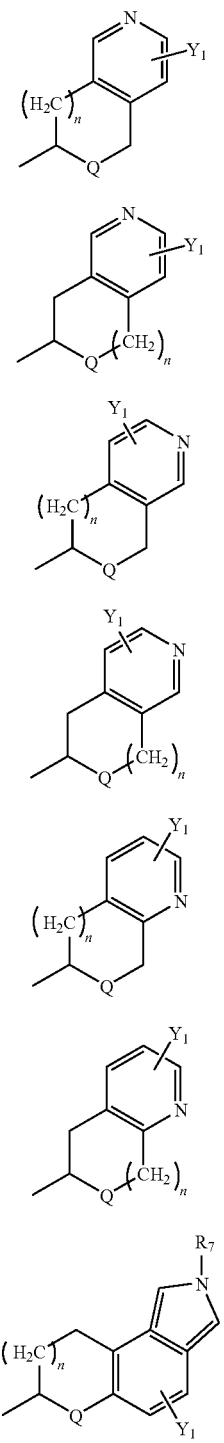

(j)

(k)

(l)

(m)

(n)

(o)

(p)

Q is CH$_2$;
X$_1$ is hydrogen, C$_{1-8}$ alkyl, C$_{3-8}$alkenyl, or C$_{3-8}$alkynyl;
X$_2$ is hydrogen, C$_{1-8}$ alkyl, C$_{3-8}$alkenyl, or C$_{3-8}$alkynyl;
or X$_1$ and X$_2$ together form =O, =S, or =NH;
R$_7$ is H, C$_{1-8}$ alkyl, CH$_2$ aryl substituted by one or more substituents Y$_1$, NR$_{10}$R$_{11}$, NHCOR$_{12}$, NHCO$_2$R$_{13}$, CONR$_{14}$R$_{15}$, CH$_2$(CH$_2$)$_n$Y$_2$, or C(=NH)NR$_{16}$R$_{17}$, R$_8$ is H, C$_{1-8}$alkyl, CH$_2$ aryl substituted by one or more substituents H, OH, Br, Cl, F, CN, CF$_3$, NO$_2$, N$_3$, C$_{1-6}$ alkyl, or CH$_2$(CH$_2$)$_n$Y$_2$'; wherein Y$_2$' is H, CF$_3$, or C$_{1-6}$alkyl;
R$_9$ is H, C$_{1-8}$ alkyl, CH$_2$ aryl substituted by one or more substituents H, OH, Br, Cl, F, CN, CF$_3$, NO$_2$, N$_3$, C$_{1-6}$ alkyl, or CH$_2$(CH$_2$)$_n$Y$_2$'; wherein Y$_2$' is H, CF$_3$, or C$_{1-6}$alkyl;
R$_{10}$ is H, C$_{1-8}$ alkyl, CH$_2$ aryl substituted by one or more substituents H, OH, Br, Cl, F, CN, CF$_3$, NO$_2$, N$_3$, C$_{1-6}$ alkyl, or CH$_2$(CH$_2$)$_n$Y$_2$'; wherein Y$_2$' is H, CF$_3$, or C$_{1-6}$alkyl;
R$_{11}$ is H, C$_{1-8}$ alkyl, CH$_2$ aryl substituted by one or more substituents H, OH, Br, Cl, F, CN, CF$_3$, NO$_2$, N$_3$, C$_{1-6}$ alkyl, or CH$_2$(CH$_2$)$_n$Y$_2$'; wherein Y$_2$' is H, CF$_3$, or C$_{1-6}$alkyl;
R$_{12}$ is H, C$_{1-8}$ alkyl, CH$_2$ aryl substituted by one or more substituents H, OH, Br, Cl, F, CN, CF$_3$, NO$_2$, N$_3$, C$_{1-6}$ alkyl, or CH$_2$(CH$_2$)$_n$Y$_2$'; wherein Y$_2$' is H, CF$_3$, or C$_{1-6}$alkyl;
R$_{13}$ is H, C$_{1-8}$ alkyl, CH$_2$ aryl substituted by one or more substituents H, OH, Br, Cl, F, CN, CF$_3$, NO$_2$, N$_3$, C$_{1-6}$ alkyl, or CH$_2$(CH$_2$)$_n$Y$_2$'; wherein Y$_2$' is H, CF$_3$, or C$_{1-6}$alkyl;
R$_{14}$ is H, C$_{1-8}$ alkyl, CH$_2$ aryl substituted by one or more substituents H, OH, Br, Cl, F, CN, CF$_3$, NO$_2$, N$_3$, C$_{1-6}$ alkyl, or CH$_2$(CH$_2$)$_n$Y$_2$'; wherein Y$_2$' is H, CF$_3$, or C$_{1-6}$alkyl;
R$_{15}$ is H, C$_{1-8}$ alkyl, CH$_2$ aryl substituted by one or more substituents H, OH, Br, Cl, F, CN, CF$_3$, NO$_2$, N$_3$, C$_{1-6}$ alkyl, or CH$_2$(CH$_2$)$_n$Y$_2$'; wherein Y$_2$' is H, CF$_3$, or C$_{1-6}$alkyl;
R$_{16}$ is H, C$_{1-8}$ alkyl, CH$_2$ aryl substituted by one or more substituents H, OH, Br, Cl, F, CN, CF$_3$, NO$_2$, N$_3$, C$_{1-6}$ alkyl, or CH$_2$(CH$_2$)$_n$Y$_2$'; wherein Y$_2$' is H, CF$_3$, or C$_{1-6}$alkyl; and
R$_{17}$ is H, C$_{1-8}$ alkyl, CH$_2$ aryl substituted by one or more substituents H, OH, Br, Cl, F, CN, CF$_3$, NO$_2$, N$_3$, C$_{1-6}$ alkyl, or CH$_2$(CH$_2$)$_n$Y$_2$'; wherein Y$_2$' is H, CF$_3$, or C$_{1-6}$alkyl
and pharmaceutically acceptable salts thereof.

2. The method of claim 1, wherein R$_6$ is a group having a formula selected from the group consisting of structures (d)-(p).

3. The method of claim 1, wherein
Y$_3$ is H;
R$_2$ and R$_3$ are each, independently, H, C$_{1-8}$ alkyl, C$_{3-8}$ alkynyl, C$_{3-8}$ alkynyl, or CH$_2$aryl substituted by one or more substituents Y$_1$; and
and pharmaceutically acceptable salts thereof.

4. The method of claim 3, wherein R$_6$ is a group having a formula selected from the group consisting of structures (d)-(p).

5. The method of claim 1, wherein
R$_1$ is C$_{1-8}$ alkyl, or one of the following structures:

Y$_3$ is H;
R$_2$ and R$_3$ are each, independently, H or C$_{1-8}$ alkyl, wherein R$_2$ and R$_3$ cannot both be H at the same time;

$R_7$ is H, $C_{1-8}$ alkyl, $CH_2$aryl substituted by one or more substituents $Y_1$, $NR_{10}R_{11}$, $NHCOR_{12}$, $NHCO_2R_{13}$, $CONR_{14}R_{15}$, or $CH_2(CH_2)_nY_2$; and and pharmaceutically acceptable salts thereof.

6. The method of claim 5, wherein $R_6$ is a group having a formula selected from the group consisting of structures (d)-(p).

7. The method of claim 1, wherein $R_1$ is $C_{1-8}$ alkyl;

$Y_2$ is H, $CF_3$, $CO_2R_9$, $C_{1-6}$ alkyl, $NR_{10}R_{11}$, $NHCOR_{12}$, $NHCO_2R_{12}$, $CONR_{13}R_{14}$, $CH_2OH$, $CH_2OR_8$, or $COCH_2R_9$;

$Y_3$ is H;

$R_2$ and $R_3$ are each, independently, H or methyl, wherein $R_2$ and $R_3$ cannot both be H at the same time;

$R_4$ is H, $C_{1-8}$ alkyl, $CO_2C_{1-8}$alkyl, or $CH_2$ aryl substituted by one or more substituents $Y_1$ and the stereocenter adjacent to $R_4$ is in an (S) configuration;

$R_5$ is H, $C_{1-8}$ alkyl, or $CH_2CO_2C_{1-8}$ alkyl;

$R_6$ is a group having a formula selected from the group consisting of structures (c) and (h)-(p); and $R_7$ is H, $C_{1-8}$alkyl, $CH_2$aryl substituted by one or more substituents $Y_1$, $NR_{10}R_{11}$, $NHCOR_{12}$, $NHCO_2R_{13}$, $CONR_{14}R_{15}$, or $CH_2(CH_2)_nY_2$; and and pharmaceutically acceptable salts thereof.

8. The method of claim 7, wherein $R_6$ is a group having a formula selected from the group consisting of structures (h)-(p).

9. The method of claim 1, wherein $R_1$ is methyl, $Y_2$ is H, $CF_3$, $CO_2R_9$, $C_{1-6}$ alkyl, $NR_{10}R_{11}$, $NHCO_2R_{12}$, $NHCO_2R_{12}$, $CONR_{13}R_{14}$, $CH_2OH$, $CH_2OR_8$, or $COCH_2R_9$;

$Y_3$ is H;

$R_2$ and $R_3$ are each H or methyl, such that when $R_2$ is H, $R_3$ is methyl and vice versa;

$R_4$ is $C_{1-8}$ alkyl, or $CO_2C_{1-8}$ alkyl, and the stereocenter adjacent to $R_4$ has a configuration of (S);

$R_5$ is H;

$R_7$ is H, $C_{1-8}$ alkyl, $CH_2$ aryl substituted by one or more substituents $Y_1$, or $CH_2(CH_2)_nY_2$; and and pharmaceutically acceptable salts thereof.

10. The method of claim 9, wherein $R_6$ is a group having a formula selected from the group consisting of structures (d)-(p).

11. The method of claim 1, further comprising administering L-dopa to the subject.

12. The method of claim 1, wherein the compound is administered orally, intraveneously, or intramuscularly.

13. The method of claim 1, wherein the compound is administered in a form selected from the group consisting of tablets, capsules, troches, powders, solutions, dispersions, emulsions and suspensions.

* * * * *